United States Patent [19]

Christ et al.

[11] Patent Number: 5,228,449

[45] Date of Patent: Jul. 20, 1993

[54] SYSTEM AND METHOD FOR DETECTING OUT-OF-HOSPITAL CARDIAC EMERGENCIES AND SUMMONING EMERGENCY ASSISTANCE

[75] Inventors: Athanasios G. Christ, 7209 Marc Dr., Falls Church, Va. 22042; John Christ, Astoria, N.Y.; James M. Childers, IV, Yorktown, Va.

[73] Assignee: Athanasios G. Christ, Falls Church, Va.

[21] Appl. No.: 644,227

[22] Filed: Jan. 22, 1991

[51] Int. Cl.$^5$ .............................................. A61B 5/026
[52] U.S. Cl. ...................................... 128/691; 128/690
[58] Field of Search ............................. 128/690-691, 128/696, 202-205, 709-710, 903; 364/413.06

[56] References Cited

U.S. PATENT DOCUMENTS

| | | | |
|---|---|---|---|
| 2,684,278 | 7/1954 | Marchand | 346/33 |
| 3,426,150 | 2/1969 | Tygart | 179/2 |
| 3,478,344 | 11/1969 | Schwitzgebel et al. | 340/312 |
| 3,517,662 | 6/1970 | Finch et al. | 128/2.06 |
| 3,572,316 | 3/1923 | Vogelman et al. | 128/2.05 |
| 3,613,670 | 10/1971 | Edenhofer | 128/2.06 F |
| 3,646,930 | 3/1972 | Patterson et al. | 128/2.06 F |
| 3,724,455 | 4/1973 | Unger | 128/2.06 A |
| 3,774,594 | 11/1973 | Huszar | 128/2.06 R |
| 3,792,700 | 2/1974 | Sarnoff et al. | 128/2.06 R |
| 3,806,936 | 4/1974 | Koster | 343/113 PT |
| 3,838,684 | 10/1974 | Manuel et al. | 128/2.05 P |
| 3,858,574 | 1/1975 | Page | 128/2.05 T |
| 3,866,204 | 2/1975 | Barkley | 340/279 |
| 3,902,478 | 9/1975 | Konopasek et al. | 128/2.06 F |
| 3,908,636 | 9/1975 | Page | 128/2.05 T |
| 3,910,260 | 10/1975 | Sarnoff et al. | 128/2.06 R |
| 3,972,320 | 8/1976 | Kalman | 128/2.1 X |
| 3,989,900 | 11/1976 | Dibner | 179/5 P |
| 4,009,708 | 3/1977 | Fay, Jr. | 128/2.05 P |
| 4,018,219 | 4/1977 | Hojaiban | 128/2.06 A |
| 4,030,483 | 6/1921 | Stevens | 128/2.05 T |
| 4,063,410 | 12/1977 | Welling | 58/38 R |
| 4,064,368 | 12/1977 | Dibner | 179/5 R |

(List continued on next page.)

FOREIGN PATENT DOCUMENTS

| | | |
|---|---|---|
| 2517453 | 4/1975 | Fed. Rep. of Germany. |
| 2922542 | 4/1980 | Fed. Rep. of Germany. |
| 2386875 | 4/1977 | France. |
| 2420333 | 3/1978 | France. |
| 810730 | 3/1959 | United Kingdom. |

OTHER PUBLICATIONS

Article appearing in *Business Week* p. 77 on Apr. 30, 1990 Entitled "This Band on the Hand Could Be a Lifesaver" Edited by Robert Buderi.

*Primary Examiner*—William E. Kamm
*Attorney, Agent, or Firm*—Sixbey, Friedman, Leedom & Ferguson

[57] ABSTRACT

A monitoring system uses infrared photoplethysmography to monitor the pulse of a person wearing a wrist unit, and the wrist unit sends RF signals which describe his heart condition to a base unit. If the wrist unit detects a cardiac arrest or if the wearer manually signals an emergency, both the wrist and the base units sound local alarms. The base unit also telephones others outside of the user's home to alert them to the emergency. The wrist unit is designed to be fail-safe and to prevent false alarms. When the wrist unit fails to detect a pulse, it makes several further attempts to detect a pulse before signalling a cardiac arrest emergency. A prioritization and output activation circuit activates wrist unit outputs, including audio signals, an RF signal transmitter, and a display, according to a predetermined priority when more than one condition requiring a response exists. RF signals sent by the wrist unit's RF signal transmitter are received by the base unit's antenna and processed to selectively activate an external display panel, two audio signal devices, and an auto dialer. The base unit also includes a removable, self-contained CPR instructions player which provides interactive real time directions for performing cardiopulmonary resuscitation.

203 Claims, 9 Drawing Sheets

U.S. PATENT DOCUMENTS

| | | | |
|---|---|---|---|
| 4,086,916 | 5/1978 | Freeman et al. | 128/2.05 T |
| 4,100,536 | 7/1978 | Ball et al. | 340/207 R |
| 4,120,294 | 10/1978 | Wolfe | 128/690 |
| 4,129,125 | 12/1978 | Lester et al. | 128/2.05 R |
| 4,178,916 | 12/1979 | McNamara | 128/734 |
| 4,195,642 | 4/1980 | Price et al. | 128/689 |
| 4,202,350 | 5/1980 | Walton | 128/690 |
| 4,224,948 | 9/1980 | Cramer et al. | 128/690 |
| 4,230,127 | 10/1980 | Larson | 128/706 |
| 4,256,117 | 3/1981 | Perica et al. | 128/690 |
| 4,258,719 | 3/1981 | Lewyn | 128/690 |
| 4,260,951 | 4/1981 | Lewyn | 328/165 |
| 4,280,506 | 7/1981 | Zurcher | 128/690 |
| 4,301,808 | 11/1981 | Taus | 128/687 |
| 4,305,401 | 12/1981 | Reissmueller et al. | 128/697 |
| 4,312,358 | 1/1982 | Barney | 128/670 |
| 4,394,777 | 7/1983 | Wren | 455/99 |
| 4,406,290 | 9/1983 | Walbeoffe-Wilson et al. | 128/689 |
| 4,407,295 | 10/1983 | Steuer et al. | 128/670 |
| 4,459,992 | 7/1984 | Gwyn | 128/687 |
| 4,489,731 | 12/1984 | Baumberg | 128/690 |
| 4,491,970 | 1/1985 | LaWhite et al. | 455/100 |
| 4,531,527 | 7/1985 | Reinhold, Jr. et al. | 128/696 |
| 4,583,524 | 4/1986 | Hutchins | 128/1 R |
| 4,807,639 | 2/1989 | Shimizu et al. | 128/690 |
| 4,819,860 | 4/1989 | Hargrove et al. | 228/668 |
| 4,827,943 | 5/1989 | Bornn et al. | 128/668 |
| 4,829,285 | 5/1989 | Brand et al. | 340/573 |

SYSTEM AND METHOD FOR DETECTING OUT-OF-HOSPITAL CARDIAC EMERGENCIES AND SUMMONING EMERGENCY ASSISTANCE

BACKGROUND OF THE INVENTION

Because of advancements in emergency cardiac care and the proliferation of pre-hospital advanced life support services, it is now possible for out-of-hospital heart attack victims to survive attacks which would have resulted in certain death in the past. However, the efficacy of any such emergency care decreases dramatically as the time interval from the onset of the heart attack to the beginning of treatment increases. Rapid care is most urgently required in cases of cardiac arrest, where treatment must begin almost immediately after the attack if the victim is to be resuscitated. Yet, in all cardiac arrests and in many other types of serious heart attacks, the victim is incapacitated and cannot summon assistance. Therefore, if a serious heart attack is not witnessed, help will probably not arrive promptly and the victim will probably not survive.

Since almost all heart attacks occur outside of the hospital and since out-of-hospital cardiac arrests account for most of the heart attack deaths, the inventors have noted that persons significantly at risk of suffering a heart attack, such as persons with a history of heart trouble and the elderly, could benefit from a system designed for continuous everyday use outside of the hospital which automatically summons aid in case of a cardiac arrest and which provides its users with a way to manually signal for aid in other types of cardiac and non-cardiac emergencies. Preferably, such a system would perform these functions without restricting freedom of movement or interfering with the user's daily routine.

Hospital cardiac care units now routinely attach heart monitors to their patients These hospital monitoring systems can immediately summon aid in case of a cardiac emergency, but they are not designed for comfort and are thus inappropriate for everyday use outside of the hospital A typical monitoring system consists of a box-like monitoring device which obtains heart function data from electrodes that are attached to a patient's chest by adhesive patches and are connected to the monitoring device by wires. The monitoring device transmits the heart function information to a central station, either through more wires or by radio frequency (RF) signals. One such system is described in U.S. Pat. No. 3,902,478 to Konopasek et al. Other systems, such as the one described in U.S. Pat. No. 4,827,943 to Bornn et al. require that the patient wear a bulky vest-like device. However, along with being burdensome for any normally active person who is not in the hospital, such monitoring systems are often troubled by false alarms.

A number of systems have been proposed which fit on a person's wrist and determine heart functions by checking the wearer's pulse. These systems typically have transmitters which signal an alarm in the event of a cardiac emergency. Such systems are shown in U.S. Pat. Nos. 3,927,320 to Kalman, No. 4,819,860 to Hargrove et al., and No. 3,572,316 to Vogleman et al. Such systems use various types of sensors which are attached to the wrist to calculate pulse rates, including pressure sensors (U.S. Pat. No. 4,406,290), sonic sensors (U.S. Pat. No. 4,489,731), and electrode-type sensors (U.S. Pat. No. 4,120,294). A relatively new method of detecting a person's pulse by using infrared light is disclosed by Cramer et al. in U.S. Pat. No. 4,224,948 and is also referred to in U.S. Pat. No. 4,819,860. In this method, infrared light is beamed onto the palm side of the wrist and the change in the intensity of light that is reflected into a detector is used to calculate a person's blood flow and thus his pulse rate. Yet, while these wrist-based systems are less burdensome than some other types of cardiac monitors, no system known to the inventors has the desired attributes and is further primarily designed for use in the home, where almost all heart attacks occur.

Some less-sophisticated in-home monitoring devices have been proposed For example, U.S. Pat. No. 4,829,285 to Brand et al. and U.S. Pat. No. 3,866,204 to Barkley disclose systems having a portable device with a tilt switch. If the user collapses, an alarm signal is sent to a fixed station. Yet, such systems can produce many false alarms or fail to cause an alarm when a heart attack occurs since they do not actually monitor heart function. Other in-home systems are comprised of a portable unit, which is often worn around the neck, and a stationary unit. If the person wearing the portable unit presses its button, the portable unit will send an RF signal to the stationary unit. This RF signal drives the stationary unit to call a central station, and the operator who answers the telephone call tries to communicate with the user of the system through a speakerphone to determine if assistance should be sent to the user's home. Components of such systems are shown generally in U.S. Pat. Nos. 3,989,900, 4,064,368, and 4,491,970. Although such systems are advertised as helpful for heart attacks, they are completely ineffective in bringing cardiac arrest victims faster help because these victims are unable to press the button to signal for help before they become unconscious.

In addressing all of the shortcomings of the previously proposed systems, the inventors have determined that the ideal out-of-hospital monitoring and warning system would include an accurate and unobtrusive pulse monitor, a miniaturized, fail-safe transmitter capable of transmitting automatically and manually-generated emergency signals, and a device for receiving the emergency signals and automatically alerting the appropriate rescue parties. However, so far as the inventors are aware, none of the known systems provide all these functions in a convenient, reliable, and affordable manner. Specifically, none of the systems described above combine obstrusive, energy-efficient, and false-alarm proof wrist-mounted pulse detection systems with miniaturized fail-safe emergency signal transmitters and dedicated base units that monitor the transmissions and summon help automatically when necessary even if the victim is outside of the hospital.

SUMMARY OF THE INVENTION

Therefore, it is a broad object of the present invention to provide a system for monitoring the physiological condition of a user and for indicating when the user's physiological condition has deteriorated.

A general object of the present invention is to provide a system that continuously monitors cardiac function, summons aid automatically in case of a cardiac arrest and allows its user to signal manually for aid in other cardiac and non-cardiac emergencies.

Another general object of the present invention is to provide a system for monitoring the physiological condition of a user which produces the fastest medical response to a cardiac failure possible outside a hospital setting.

Another general object of the present invention is to provide a system designed to be used primarily outside the hospital that continuously monitors cardiac function, summons aid automatically in case of a cardiac arrest and allows its user to signal manually for aid in other cardiac and non-cardiac emergencies, and performs these functions without troubling its user with false alarms or restricting the user's lifestyle in the process.

Another object of the present invention is to provide a system for monitoring the physiological condition of a user which includes a unit worn on the arm and a base unit.

A further object of the present invention is to provide a system for monitoring the physiological condition of a user which includes monitor means, designed to be worn on the user's arm, for detecting a physiological condition and transmitting periodic wireless signals representing the condition, and a base unit which receives the signals and has indicating means for summoning assistance when no signals are received by the base unit.

It is also an object of the present invention to provide a system for monitoring the physiological condition of a user which includes monitor means, designed to be worn on the user's arm, for detecting a physiological condition and transmitting periodic wireless signals representing the condition, and a base unit which receives the signals and has indicating means for summoning assistance when some portion of the system has failed or is failing.

Another object of the present invention is to provide a system for monitoring the physiological condition of a user which includes monitor means, designed to be worn on the user's arm, for detecting a physiological condition and transmitting periodic wireless signals representing the condition, and a base unit which receives the signals and has indicating means for summoning assistance when the signals received by the base unit indicate a health problem.

A further object of the present invention is to provide a system for monitoring the physiological condition of a user which includes monitor means, designed to be worn on the user's arm, for detecting a physiological condition and transmitting periodic wireless signals representing the condition, and a base unit means having indicating means for summoning assistance, with the monitor means including an attachment sensor which produces an indication when the monitor means is not attached properly to the user's arm.

It is another object of the present invention to provide a monitoring system which noninvasively detects a user's cardiac function and summons assistance in case of cardiac dysfunction.

A further object of the present invention is to provide a system for monitoring the blood flow of a user and summoning assistance when a problem is detected with blood flow which uses infrared emitters and detectors to sense the flow of blood.

Another important object of the present invention is to provide a system for monitoring the physiological condition of a user which includes an unobtrusive monitor means, designed to be worn on the user's arm, for detecting a physiological condition and transmitting wireless signals representing the condition, and a base unit which receives the signals and has indicating means for summoning assistance, which is relatively inexpensive and readily useful in non-hospital environments and which will not prevent the user from living life in a normal fashion.

Yet another object of the present invention is to provide a system which monitors a user's cardiac function and automatically summons assistance upon detecting a dysfunction and which also has activation means manually operable by the user of the monitor means to summon assistance.

A further object of the present invention is to provide a system for monitoring the physiological condition of a user which includes monitor means, designed to be worn on the user's arm, for detecting a physiological condition and transmitting periodic wireless signals representing the condition, and a base unit having indicating means for summoning assistance, wherein the monitor means operates using rechargeable batteries which are recharged by the base unit.

Yet another object of the present invention is to provide a system for monitoring the physiological condition of a user which includes monitor means, designed to be worn on the user's arm, for detecting a physiological condition and transmitting periodic wireless signals representing the condition, and a base unit which receives the signals and has indicating means for summoning assistance, with the base unit operating to store and charge one or more monitor means.

A further object of the present invention is to provide a system for monitoring the physiological condition of a user which includes monitor means, designed to be worn on the user's arm, for detecting a physiological condition and transmitting periodic wireless signals representing the condition, and a base unit which receives the signals and has indicating means for summoning assistance, where the base unit and monitor means are substantially fail-safe and where the base unit and monitor means also operate to prevent false alarms.

It is also an object of the present invention to provide a system for monitoring the physiological condition of a user which includes monitor means, designed to be worn on the user's arm, for detecting a physiological condition and transmitting periodic wireless signals representing the condition, and a base unit which receives the signals and has a mechanism for automatically delivering a message to a remote location using a public communications network when appropriate.

Yet another object of the present invention is to provide a system for monitoring the physiological condition of a user which includes monitor means, designed to be worn on the user's arm, for detecting a physiological condition and transmitting periodic wireless signals representing the condition, and a base unit which receives the signals and has indicating means for summoning assistance, where the system operates to assist the user in determining the transmission range of the monitor means to the base unit.

A related object of the present invention is to provide a system of the described type which allows a user to determine the transmission range of a monitor means, wherein an output response of the base unit to signals transmitted by the monitor means depends on the strength of the signals received.

A further object of the present invention is to provide a system for monitoring the physiological condition of a user which includes monitor means worn by the user for detecting a physiological condition and periodically transmitting one of a group of wireless signals representing the condition, and a base unit which receives the signals and has indicating means for summoning assistance, wherein the monitor means selects the one signal to be transmitted according to a predetermined priority whenever more than one of the possible signals are accurate in light of the operational and physiological conditions determined by the monitor means.

Another object of the present invention is to provide a cardiac monitoring system including a single base unit which selectively responds to one or more monitor units worn by users.

Yet another object of the present invention is to provide a cardiac monitoring system which has a base unit monitoring one or more monitor units, with the monitor units transmitting signals coded to identify the transmitting monitor unit.

A further object of the present invention is to provide a system for monitoring the physiological condition of a user which includes wrist-mounted monitor means for detecting a physiological condition and transmitting wireless signals representing the condition, and a base unit which receives the signals and has indicating means for summoning assistance, with the monitor means having the style, appearance and function of a wristwatch.

It is also an object of the present invention to provide a system for monitoring the physiological condition of a user which includes monitor means, designed to be worn on the user's arm, for detecting a physiological condition and transmitting periodic wireless signals representing the condition, and a base unit which receives the signals and has indicating means for summoning assistance, such that the monitor means and base unit are protected against power failures by appropriate backup batteries and battery charge sensing circuits.

Another object of the present invention is to provide a system for monitoring the physiological condition of a user which includes monitor means, designed to be worn on the user's arm, for detecting blood flow using infrared emitters and detectors, wherein the infrared emitters are pulsed in operation to conserve power.

Yet another object of the present invention is to provide a device worn by a user which detects defibrillatory shocks and indicates when such a shock has been received.

A further object of the present invention is to provide a system for monitoring the physiological condition of a user which includes monitor means, designed to be worn on the user's arm, for detecting a cardiac condition and transmitting wireless signals representing the condition, and a base unit which receives the signals and has indicating means for summoning assistance, where the monitor means prevents false alarms by signalling cardiac problems only after a problem has been detected continuously over a specified time period.

Yet another object of the present invention is to provide a system which monitors blood flow using infrared emitters and detectors, using splitting devices in conjunction with the emitters so that infrared radiation from a single emitter is transmitted to a plurality of locations.

A further object of the present invention is to provide a system which monitors blood flow using a plurality of infrared emitters and detectors, which operates in a power saving mode to activate only certain of the emitters when these emitters produce a sufficient measurement of blood flow.

Yet another significant object of this invention is to provide a system which monitors the cardiac function of a user and provides alarms in multiple zones upon detecting a problem, with the zones being for example (1) at the immediate location of the user, (2) at the location of a base unit in the immediate area positioned to broadcast an alarm to persons who can provide immediate aid, and (3) at a remote location from which skilled medical assistance can be dispatched.

Another object of the present invention is to provide a system for monitoring the physiological condition of a user which produces the fastest medical response to a cardiac failure possible outside a hospital setting by continuously monitoring cardiac function and sounding zoned alarms which will inform the user of a problem, inform caregivers in the immediate vicinity that assistance is needed, and inform ambulance dispatchers at a remote location that help is needed.

Another major object of the present invention is to provide a device for instructing a caregiver in the provision of emergency aid.

It is a further object of the present invention to provide a health maintenance information device for providing emergency instructions such as CPR instructions and information to a caregiver in case of a downturn in the user's physiological condition.

Another object of the present invention is to provide a system for monitoring the physiological condition of a user which produces the fastest medical response to a cardiac failure possible outside a hospital setting by continuously monitoring cardiac function and sounding zoned alarms which will inform the user of a problem, inform caregivers in the immediate vicinity that assistance is needed, and inform ambulance dispatchers at a remote location that help is needed, which further includes a portable device which will provide emergency instructions to the caregivers in the immediate vicinity so that they can perform emergency procedures during the period following the detection of a cardiac problem and prior to the arrival of an ambulance.

It is also an object of the present invention to provide a portable device for giving real time instructions for the performance of emergency medical techniques which operates interactively, repeating instructions or pausing as necessary until the caregiver indicates a readiness to proceed.

Another object of the present invention is to provide a portable digital speech processing system which gives real time, interactive instructions for the performance of cardiopulmonary resuscitation or other emergency medical techniques which is capable of giving both preparatory instructions and rhythmic or timing instructions during the actual administration of CPR.

These objects and others are achieved by providing a monitoring system with two parts—a portable battery-powered wrist unit and a base unit. The wrist unit monitors the condition of the wearer's heart by using infrared photoplethysmography to monitor his pulse and sends RF signals which describe his heart condition to a base unit. If the wrist unit detects a cardiac arrest or if the wearer manually signals an emergency, both the wrist and the base units sound local alarms. The base unit also telephones others outside of the user's home to alert them to the emergency.

The wrist unit monitors its wearer's pulse by causing its infrared light emitters to shine infrared light into capillaries in the palm side of the wearer's wrist and then using its photosensors to detect how much of this light is absorbed. Because more infrared light is absorbed as more blood flows through the capillaries, the wrist unit's pulse determination module uses this light absorption information to determine if a pulse exists. When it detects a pulse, the pulse determination module notifies the wrist unit's timer module. The timer module decides if the wearer's heart is functioning normally, basing this decision on whether or not it receives a set number of pulse readings from the pulse determination module over a time interval, and then relays its decision to the wrist unit's prioritization and output activation module. The prioritization and output activation module prioritizes any messages that it receives and activates the wrist unit's output devices: an audio signal device, an RF signal transmitter, and a display device such as an LCD. The prioritization and output activation module responds appropriately to the most important message that it receives. These output devices provide a localized warning during emergencies.

RF signals sent by the wrist unit's RF signal transmitter are received by the base unit's antenna and processed by the base unit's RF signal decoder. The decoded message is then sent to the base unit's microcontroller, which determines the base unit's response to all incoming information and activates the base unit's output devices accordingly. These output devices include an external display panel which may be a light emitting diode (LED) display, two audio signal devices, and an auto dialer which can call several preprogrammed telephone numbers and deliver different prerecorded messages.

The base unit also includes a removable, self-contained CPR instructions player which provides interactive real time directions for performing cardiopulmonary resuscitation or other appropriate emergency medical techniques.

DETAILED DESCRIPTION OF A PREFERRED EMBODIMENT

Figure 1:
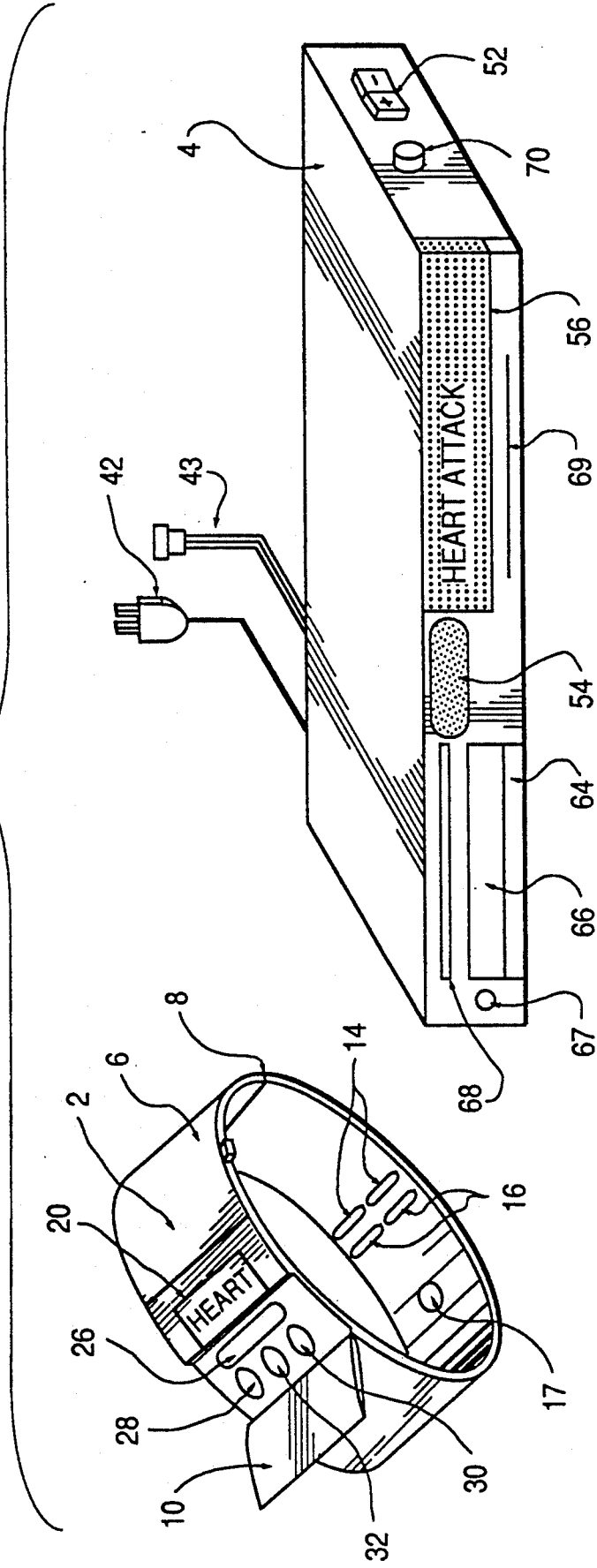
FIG. 1 is an illustration showing the wrist and base units of the present invention.

As shown in FIG. 1, the present invention comprises a portable wrist unit 2 and a stationary base unit 4. The wrist unit 2 monitors the heart condition of its wearer by monitoring his pulse and sends RF signals to the base unit 4 which notify the base unit 4 of both the wearer's heart condition and the operational status of the wrist unit 2. If the wrist unit 2 detects a cardiac arrest, the wearer of the wrist unit 2 manually signals another type of emergency, or the wrist unit 2 malfunctions, both the wrist unit 2 and the base unit 4 will sound local alarms to alert people in the wearer's home of the emergency or operational problem, as appropriate. The base unit 4 will also call pre-programmed telephone numbers and deliver prerecorded messages to alert people outside of the wearer's home when cardiac arrests or manually-signalled emergencies are indicated by the wrist unit 2.

The wrist unit 2 has a strap 6 which is adapted to clamp the wrist unit 2 to the wearer's forearm or wrist. The strap 6 includes a clasp 8, which is preferably a positive latch-type mechanism, that connects the ends of the strap 6 to hold the wrist unit 2 on the wearer's arm. The strap 6 may be adjustable or may be custom-made for the user. The wrist unit 2 is provided with a hinged door 10 (shown in the open position in FIG. 1) which the wearer can easily open but which is designed not to open accidentally. Directly behind the hinged door 10 is an inner compartment which contains several buttons operable by the wearer: an on/off button 26, a manual heart attack button 28, an other emergency button 30, and a range determining feature button 32. The functions performed by these buttons are explained below. The wrist unit 2 also has infrared light emitters 14, photosensors 16, a defibrillation sensor 17 (which may comprise, for example, a stainless steel electrode), and a display device 20 (which is an external liquid crystal display).

Figure 2:
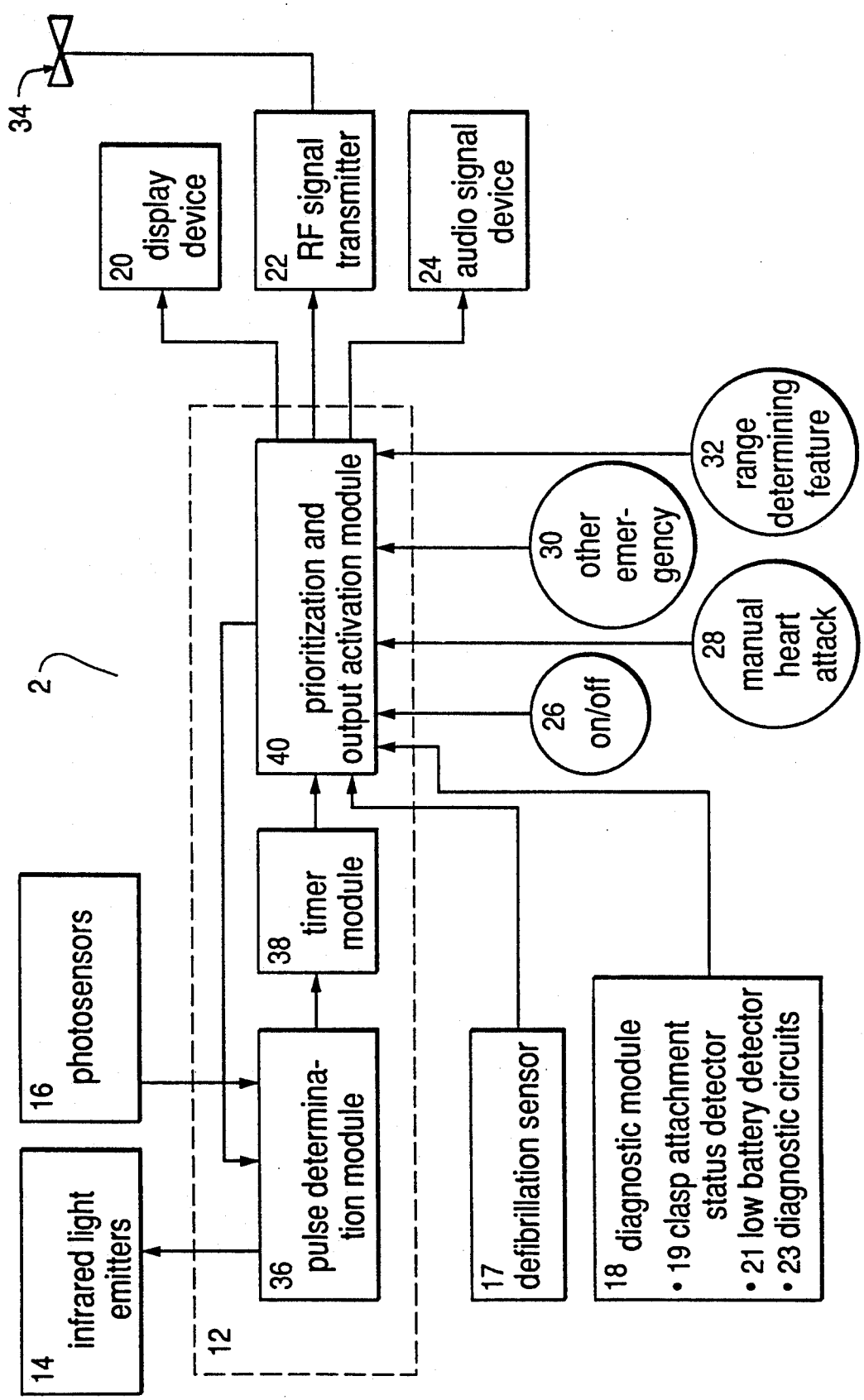
FIG. 2 is a block-schematic diagram of the wrist unit of the present invention.

FIG. 2 shows in block form the components of the wrist unit 2. Besides the infrared light emitters 14, photosensors 16, defibrillation sensor 17, display device 20, on/off button 26, manual heart attack button 28, other emergency button 30, and range determining feature button 32, the wrist unit 2 contains a microcontroller 12, a diagnostic module 18 (which monitors the operation of the wrist unit 2 and indicates malfunctions), an RF signal transmitter 22, an audio signal device 24 (which is a piezoelectric buzzer), and an antenna 34. The microcontroller 12, which receives messages from various sources in the wrist unit and sends out messages which control the wrist unit's output devices, implements a pulse determination module 36, a timer module 38, and a prioritization and output activation module 40. Power for the components of the wrist unit 2 comes from one or more removable and rechargeable batteries, a power regulator, and a power controller which are conventional and are not shown in the drawings. Finally, since the wrist unit 2 is designed for continuous everyday use at home, it will preferably be constructed of materials such that it will be waterproof, shockproof, chemically inert, and resistant to changes in temperature. For the convenience of the user and to make it less obtrusive, the wrist unit 2 preferably also provides a time-of-day indication through the display device 20. The wrist unit 2 may also implement other features normally associated with digital wristwatches.

The microcontroller 12 may be a microcontroller or microprocessor and preferably comprises input/output ports, timing devices, permanent program storage memory, and program-responsive circuitry which functions as a processor. Microcontroller 12 may also include random access memory. The microcontroller 12 can be implemented using any number of conventional circuits in one or more integrated packages. It is generally preferred, because of size, weight, and power consumption constraints on the wrist unit 2, that a microcontroller which integrates at least most of these functions into a single package be selected for this application. It will be noted that the microcontroller 12 implements a plurality of independent programs which must run concurrently in real time, including the pulse determination module 36, general timing functions provided by the timer module 38, and the prioritization and output activation module 40. If a single integrated microcontroller 12 is used, the various independent functions may be implemented in a time-sharing or interrupt-driven manner as is well known in the art; otherwise, independent circuits may be used to implement these various features.

Figure 3:
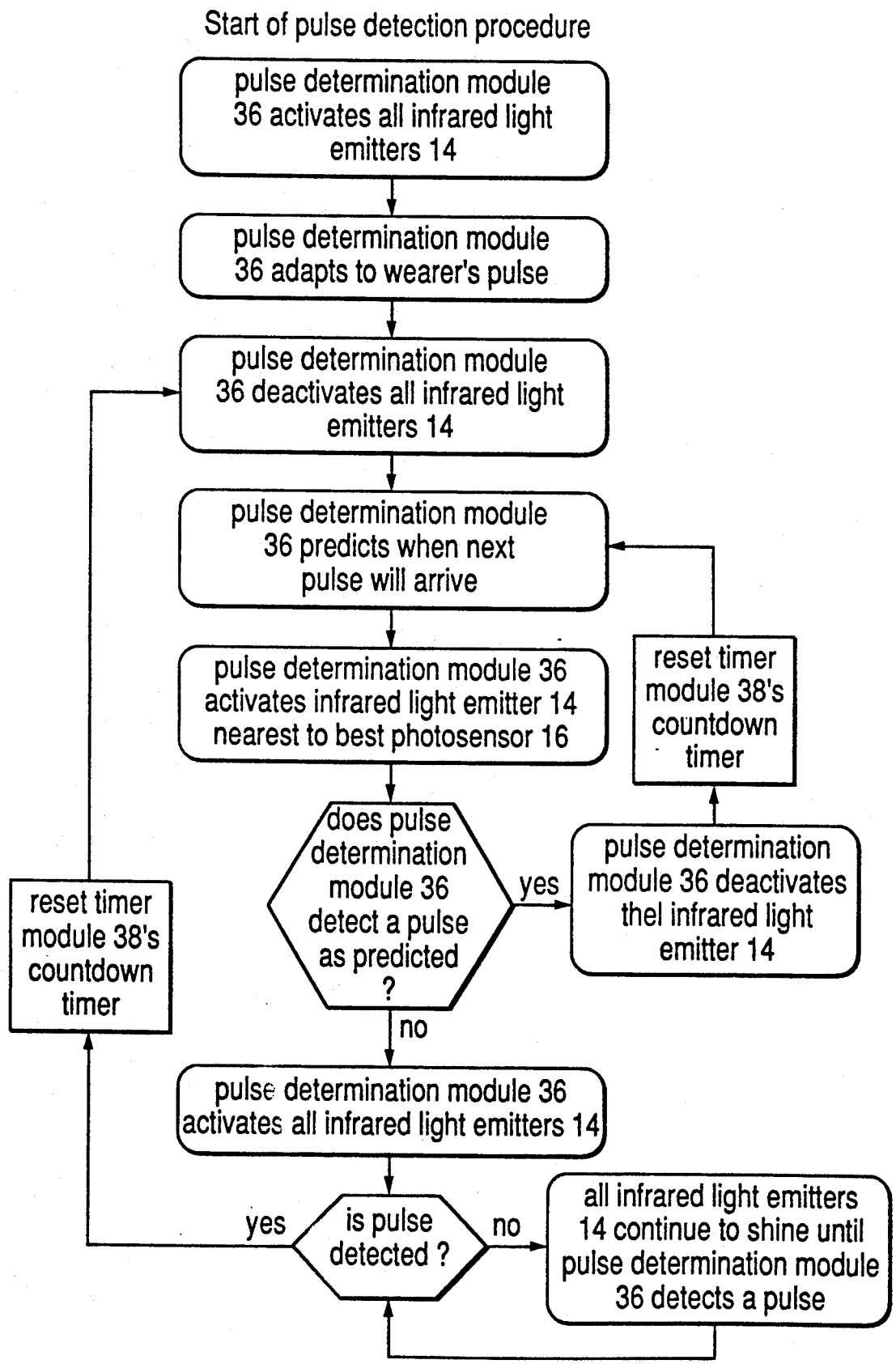
FIG. 3 is a flow diagram of the pulse detection procedure followed by the wrist unit of the present invention.
Figure 5:
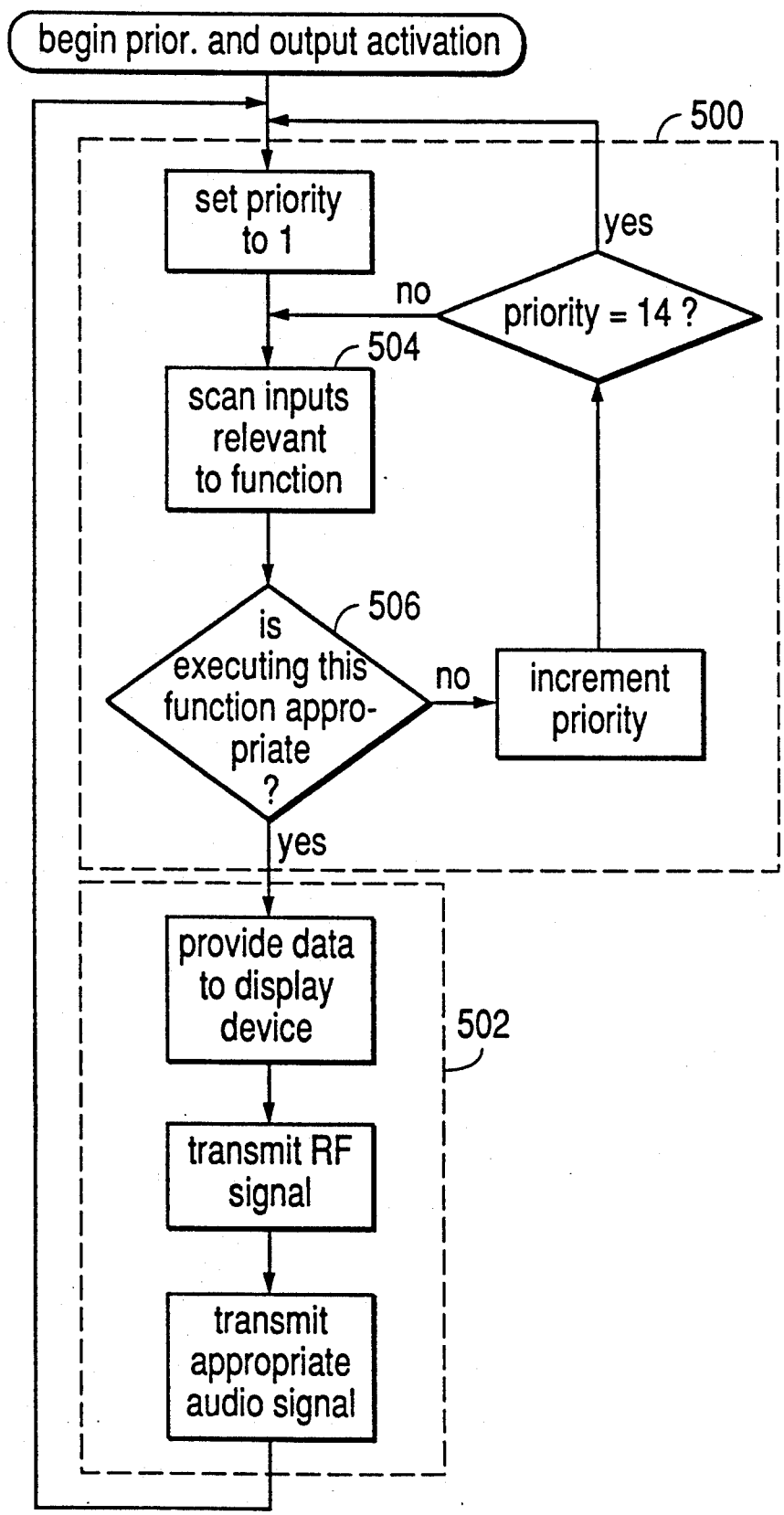
FIG. 5 is a flowchart showing the operation of the prioritization and output activation section of the wrist unit of the present invention.

The microcontroller 12 will implement software according to the descriptions of the operation of wrist unit 2 contained herein, with particular reference to the flowcharts of FIGS. 3 and 5 and the various tables in the specification showing the prioritization of output signals and specifying system responses to particular situations. This software will be described later in more detail.

The infrared emitters 14 are connected to and controlled by the pulse determination module 36. The photosensors 16 are connected as inputs to the pulse determination module 36. The pulse determination module 36 is connected as an input to the timer module 38. The timer module 38, defibrillation sensor 17, diagnostic module 18, on/off button 26, manual heart attack button 28, other emergency button 30, and range determining feature button 32 are operably connected as inputs to the prioritization and output activation module 40. The display device 20, RF signal transmitter 22, and audio signal device 24 are operably connected as output devices of the prioritization and output activation module 40. The prioritization and output activation module 40 is also connected to and controls the pulse determination module 36. The antenna 34 is operably connected to the RF signal transmitter 22.

The wrist unit detects the wearer's pulse by using infrared photoplethysmography to determine his blood flow. The wrist unit's pulse determination module 36 activates one or more infrared light emitters 14 to shine infrared light into capillaries in the palm side of the wearer's forearm or wrist. This infrared light is absorbed by the blood flowing in the wearer's circulatory system, and one or more photosensors 16 detect changes in the absorption of this light due to differing amounts of blood flow. The photosensors 16 relay this light absorption information to the pulse determination module 36, which uses the information to determine the wearer's blood flow and thus his pulse rate. This method is preferred because it is an efficient and noninvasive way of detecting the presence or absence of venous and/or arterial blood flow.

The operation of the pulse determination module 36 of microcontroller 12 is shown in the flowchart of FIG. 3. It should be noted that the pulse determination module 36 will be activated only when the wrist unit 2 is in an active mode, i.e. activated for pulse detection. This state will also be referred to as "turned on." As can be seen in the flowchart of FIG. 3, the pulse determination module 36 initially adapts to the wearer's pulse by activating all the infrared light emitters 14 (only two emitters are shown in FIG. 1, but more may be implemented) so that the photosensors 16 can provide complete light absorption information to the pulse determination module 36. The pulse determination module 36 uses this information to approximate the frequency of the wearer's pulse. Once it determines the pulse frequency, the pulse determination module 36 shuts off the infrared light emitters 14. The pulse determination module 36 then predicts when the wearer's next pulse will result. Shortly before this next pulse is expected, the pulse determination module 36 activates the infrared light emitter 14 closest to the photosensor 16 which provided the most conclusive infrared light absorption information (or the strongest pulse signal) during the previous pulse detection attempt. Once the pulse determination module 36 detects the next pulse, it shuts off the infrared light emitter 14. The pulse determination module 36 then again predicts when the next pulse will result, activates the appropriate infrared light emitter 14 shortly before the next pulse is scheduled to arrive, and deactivates this infrared light emitter 14 after it detects this pulse. The pulse determination module 36 will continue to repeat this procedure as long as the wearer's pulse is detected as predicted.

However, if no pulse is detected a short time after the pulse determination module 36 predicted that it should have arrived, for example two seconds, the pulse determination module 36 activates all of the infrared light emitters 14. All infrared light emitters 14 then continue to function until the next pulse is detected. If a subsequent pulse is found, the pulse determination module 36 shuts off all the infrared light emitters 14 and resumes the normal procedure of periodically activating only the infrared light emitter 14 closest to the photosensor 16 which provided the best infrared light absorption information during the previous pulse detection attempt.

In a preferred embodiment of the wrist unit 2, two additional features are implemented to conserve the wrist unit's battery during the pulse detection procedure. First, the infrared light emitters 14 may be quickly flashed or strobed one or more times when they are activated rather than being powered continuously when they are activated. That is, the emitters 14 may be operated at less than a full duty cycle during the period when they are activated.

Figure 4:
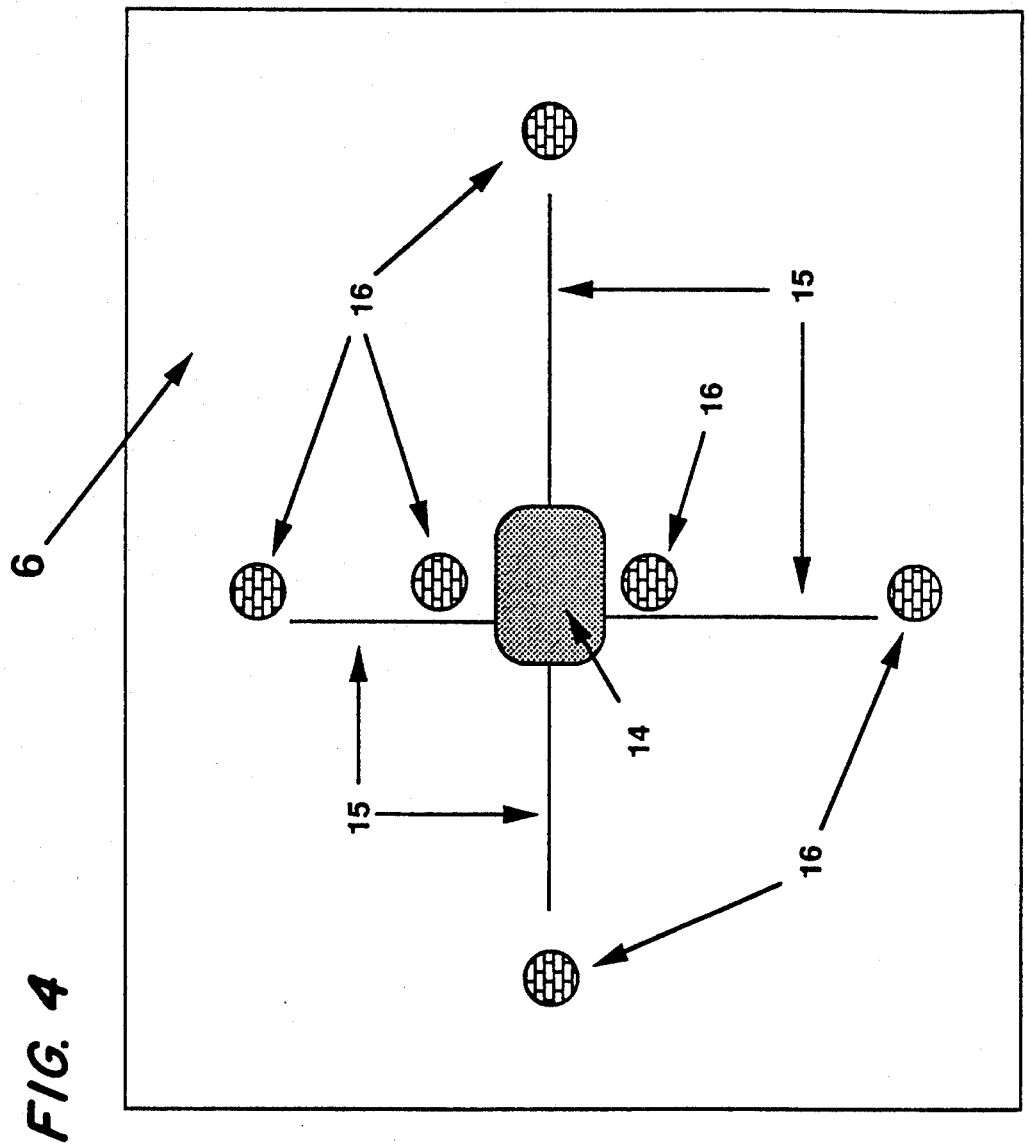
FIG. 4 is an illustration showing a preferred infrared light emitter and photosensor arrangement in the wrist unit of the present invention.

Second, as illustrated in FIG. 4, fiber optic light pipes 15 may be provided to take the infrared light from one or more central infrared light emitters 14 and disperse it near a plurality of photosensors 16. The fiber optic light pipes 15 are constructed from a light transmitting material and each have one of their ends connected to the infrared light emitter 14 for collecting infrared light waves therefrom. The second, open ends of the fiber optic light pipes may be aligned so that they are directed at the skin of the wearer of wrist unit 2 so that the infrared light is transmitted through the ends of fiber optic light pipes 15 into the capillaries of the wearer for detection by photosensors 16 adjacent to the ends of fiber optic light pipes 15. The use of light pipes to channel the light from infrared emitters 14 to a plurality of photosensors 16 permits operation of the device with fewer infrared emitters 14 than would otherwise be required to provide light to the photosensors 16. Because the infrared emitters 14 use a significant part of the overall power required by wrist unit 2, this method provides much longer battery life than would otherwise be possible.

Each time a pulse is detected, the pulse determination module 36 sends a message to the timer module 38 which prompts the timer module 38 to reset a continuously operating countdown timer which may have a duration, for example, of 15 seconds. As long as this countdown timer does not equal zero, the timer module 38 regularly signals that the wearer's heart is operating normally by sending the "pulse okay" message to the prioritization and output activation module 40 every three seconds. If the countdown timer completes its countdown, the timer module 38 signals that the wearer is in cardiac arrest by sending the "cardiac arrest" message to the prioritization and output activation module 40. The countdown timer will operate only when the wrist unit 2 is in an active mode (turned on). When the wrist unit 2 is in its deactivated mode, although other aspects of wrist unit 2 may continue to function, the pulse determination module 36 will not function to detect the wearer's pulse and the countdown timer will be set to a nonzero value and will not count down.

The countdown delay feature prevents false alarms, since during the delay, the wrist unit 2 will have several opportunities to attempt pulse detection with first one and then all of the infrared light emitters 14 activated. In particular, this delay feature, coupled with the design feature of multiple detection points at plural photosensors 16, prevents false alarms of the type which may occur when wrist unit 2 shifts position on the arm of the wearer. Such a shift in position might cause a device with a single photosensor 16 to occupy a position out of detection range of the capillary beds in the forearm, so that further pulses would not be detected. This occurence might cause an alarm even though the user's heart is functioning normally. The present system, in contrast, allows several attempts to detect a pulse. In the preferred embodiment, these attempts will take place first with a single infrared emitter 14 activated, and subsequently with all available devices activated to scan for any pulse indication. Only if a pulse is not detected when all infrared light emitters 14 are activated for a defined period of time in which several pulses should have been detected will an alarm be sounded. While this method results in a delay of a few seconds in summoning assistance, it prevents the needless dispatching of emergency equipment and avoids unnecessarily alarming the user, who will naturally be upset by an alarm indicating that his or her heart has ceased functioning. The prevention of false alarms in the system of the present invention is considered very important. The system will not achieve its desired function if it produces significant numbers of false alarms because emergency dispatchers receiving calls generated by a system prone to false alarms will not take them seriously. Thus, to maximize the user's chance of survival in case of a heart attack, the present invention provides an accurate and reliable system which will immediately prompt the dispatch of an advanced life support ambulance whenever it sounds an alarm.

As shown by numbers 26, 28, 30, and 32 in FIGS. 1 and 2, several buttons are used to control certain functions of the wrist unit 2. As soon as any of these buttons are activated, the button's message is sent to the prioritization and output activation module 40. While the activating means are described herein as "buttons," those skilled in the art will recognize that a downwardly movable momentary contact switch is only one of a large number of activating or switching devices which could be used to control operation of the wrist unit 2. For example, touch-sensitive devices or toggle switches could be used. While it is preferred for the convenience of a panic-stricken user to provide separately actuated switching means for control of these functions, it would also be possible to use other schemes for actuating functions of the wrist unit 2. As an example, two switching means might be provided, with the first permitting scrolling through a menu of function selections which would be displayed on the display device 20 of wrist unit 2, and the second switching means operating to select the displayed function. In another scheme, a single switching means could be used to actuate a plurality of functions depending on the number of times the switching means is actuated during a defined time period.

In the preferred embodiment, when the on/off button 26 is activated, it sends either the "wrist on" or "wrist off" message to the prioritization and output activation module 40 to indicate that the wearer wishes to either fully activate the wrist unit 2 or to put the wrist unit 2 into its standby mode, respectively (the wrist unit 2 is not totally deactivated even when the "wrist off" message is generated). The prioritization and output activation module 40 decides whether the on/off button 26 is sending the "wrist on" or "wrist off" message by toggling between the two states whenever the button is activated.

When the manual heart attack button 28 is activated, it sends the "manual heart attack" message to the prioritization and output activation module 40 to indicate that the wearer believes that he is having a heart attack. When the other emergency button 30 is activated, it sends the "other emergency" message to the prioritization and output activation module 40 to indicate that the wearer has signalled that a noncardiac emergency has occurred.

The range determining feature button 32 allows the wearer of the wrist unit 2 to determine the wrist unit's range of RF transmission to the base unit 4 (as will be explained in more detail below in the section relating to the base unit). When the range determining feature button 32 is activated, it sends either the "range on" or the "range off" message to the prioritization and output activation module 40 to commence or terminate the range determining feature, respectively. As in the case of the on/off button 26, the prioritization and output activation module 40 decides whether the range determining feature button 32 is sending the "range on" or "range off" message by toggling between the two messages whenever the button is activated.

When multiple switching means are provided to activate separate functions of wrist unit 2 as provided in the preferred embodiment, it becomes very important to define the response of the system when more than one of the switching means is actuated within a short time period. If any two of the wrist unit's buttons are pressed within a very short defined time period indicating that they were pressed essentially simultaneously, the inputs to prioritization and output activation module 40 are filtered so that only one input is accepted. Such filtering can be accomplished through separate circuits, if desired, as part of a debouncing and prioritization of the pushbutton inputs, or it can be performed alternatively through programming of the prioritization and output activation module 40 of microcontroller 12 to check for multiple keypresses in a short time. In the preferred embodiment, the prioritization and output activation module 40 interprets the incoming messages from two buttons that were pressed essentially simultaneously as follows:

"wrist on" (from the on/off button 26) and "manual heart attack" (from the manual heart attack button 28) becomes "wrist on;"

"wrist on" (from the on/off button 26) and "other emergency" (from the other emergency button 30) becomes "wrist on;"

"wrist off" (from the on/off button 26) and "manual heart attack" (from the manual heart attack button 28) becomes "manual heart attack;"

"wrist off" (from the on/off button 26) and "other emergency" (from the other emergency button 30) becomes "other emergency;"

"manual heart attack" (from the manual heart attack button 28) and "other emergency" (from the other emergency button 30) becomes "manual heart attack;" and "range on" or "range off" (from the range determining feature button 32) and the message from any other button becomes the other button's message.

This priority scheme recognizes that, when the wrist unit has been "turned off", or placed in a standby mode wherein many of its operations including the pulse detection operation are not active, it is more likely that the user will want to completely activate the wrist unit 2 than it is that the user will wish to summon assistance. Thus, the pressing of a plurality of buttons when the wrist unit 2 is deactivated is interpreted to mean that the user wishes to fully activate the wrist unit 2. Thus, "wrist on" signals take priority over other signals. On the other hand, when the wrist unit 2 is fully operational, it is somewhat more likely that pressing multiple buttons reflects panic or lack of motor coordination in an emergency situation. Therefore, when the wrist unit 2 is in a fully activated state, emergency signals will generally take priority over on/off signals. The range determination function button never takes priority over another button since it is designed to activate a less frequently used feature which is less critical to the user than either summoning aid or activation/deactivation.

Along with receiving messages from the timer module 38 and the wrist unit's various buttons, the prioritization and output activation module 40 receives messages from the defibrillation sensor 17 and the diagnostic module 18. The defibrillation sensor 17, which may comprise one or more stainless steel electrodes, is connected to the prioritization and output activation module 40 via a circuit which detects sudden large-magnitude voltage applications of the sort which would be detected if a defibrillator was being used on the wearer of wrist unit 2, and generates a signal in response. In general, this circuit detects and responds to a sudden large-scale increase in charge or voltage available at the electrode or electrodes. This response signal is transmitted as a "shock received" message to the prioritization and output activation module 40.

The diagnostic module 18 may be implemented using discrete components, using an independent microcontroller, using the microcontroller 12, or, preferably, using a combination of discrete components and the microcontroller 12. The diagnostic module 18 may include a clasp attachment status detection circuit 19, a low battery detector 21, and other diagnostic circuits 23. The diagnostic module 18's clasp attachment status detector 19 is preferably a switch connected to the clasp 8 that is closed when the clasp 8 is attached and open when the clasp 8 is open. The normally closed switch thus provided is more fail-safe than a normally open switch. Clasp attachment status detector 19 determines if the wrist unit 2 is properly secured to the wearer's wrist or forearm by checking that the unit's clasp 8 is properly secured. If the clasp 8 is not properly secured, the clasp attachment status detector 19 sends the "clasp open" message to the prioritization and output activation module 40. If an open clasp 8 is subsequently secured, the clasp attachment status detector 19 sends the "clasp reclosed" message to the prioritization and output activation module 40. In its simplest form, the clasp attachment status detector may be a switch connected to selectively provide a signal to an input port of microcontroller 12 based on whether the switch is closed or open. The diagnostic module 18's low battery detector 21 may be a known battery power measurement circuit that sends a signal to an input port of the microcontroller 12 when the batteries of wrist unit 2 are low. This signal will be interpreted by the microcontroller 12 as the "low wrist battery" message to the prioritization and output activation module 40 if the battery powering the wrist unit 2 falls below a specified percentage of maximum charge. The diagnostic module 18's additional independent internal diagnostic circuits 23 may be provided as desired to detect malfunctions in other components of the wrist unit 2. When these diagnostic circuits 23 detect malfunctions, the "wrist error" message is sent to the prioritization and output activation module 40.

Whenever it receives any of the aforementioned messages, the prioritization and output activation module 40 activates the wrist unit's output devices—the display device 20, the RF signal transmitter 22, and the audio signal device 24 to respond appropriately to the condition that this message is indicating. The prioritization and output activation module 40 activates the response by sending each output device the same message that it receives.

If the prioritization and output activation module 40 receives messages from several sources within a very short time or simultaneously, which will occur if more the condition is detected at about the same time, it prioritizes the incoming messages and sends signals which constitute an appropriate response to the highest priority message to the output devices. The preferred prioritization scheme is shown in Table 1:

TABLE 1

| | |
|---|---|
| priority one | "shock received" |
| priority two | "wrist off" |
| priority three | "wrist on" |
| priority four | "manual heart attack" |
| priority five | "other emergency" |
| priority six | "cardiac arrest" |
| priority seven | "wrist error" |
| priority eight | "clasp reclosed" |
| priority nine | "clasp open" |
| priority ten | "low wrist battery" |
| priority eleven | "range off" |
| priority twelve | "range on" |
| priority thirteen | "pulse okay" |

As can be seen in Table 1, the "wrist on" and "wrist off" indications are given priority over other signals because while the system will automatically signal a cardiac arrest, it is also designed to give the user the ultimate control of its operation to minimize inconveniences. For example, the user may absent-mindedly attach or detach the wrist unit from his or her body while turning it on or off. Thus, an on or off signal may frequently be closely associated in time with a failure to detect a pulse, and under these circumstances failure to detect a pulse is less likely to indicate an emergency. The pulse okay signal is given the lowest priority since it conveys information less important to the immediate operation of the system. Similarly, the range on/off and low wrist battery signals have generally lower priority than the signals indicating an emergency.

The prioritization scheme described above allows the system to alert its users to the most important condition so that they can concentrate their efforts towards rectifying the problem without being distracted by the indication of less-important conditions. This prioritization scheme also allows this critical condition to be indicated in minimum time and with minimum power. Furthermore, the prioritization scheme allows for more information to be conveyed than is suggested by the titles of the messages transmitted. For example, a "low wrist battery" message also indicates that the user of the wrist unit 2 has not experienced cardiac arrest or pressed an emergency button, since the wrist unit 2 would otherwise have transmitted the higher priority message according to Table 1.

The responses of the output devices to each highest-priority condition selected by the prioritization and output activation unit 40 will now be described in detail. The display device 20 displays "OFF" if it receives the "wrist off" message from the prioritization and output activation module 40. If the display device 20 receives the "cardiac arrest" or "manual heart attack" message, it displays "HEART." The display device 20 displays "OTHER" if it receives the "other emergency" message, "RANGE" if it receives the "range on" message, "ERROR" if it receives the "wrist error" message, "CLASP" if it receives the "clasp open" message, and "BAT" if it receives the "low wrist battery" message. The display device 20 is cleared if the prioritization and output activation module 40 sends it signals consistent with the "wrist on," "clasp reclosed," "range off," "pulse okay," or "shock received" messages. The display device 20 maintains its display (or remains cleared) until it receives another message from the prioritization and output activation module 40.

Whenever the RF signal transmitter 22 receives a signal from the prioritization and output activation module 40 indicating that a signal other than "range off," is appropriate, it immediately sends a coded RF signal transmission of that message to the base unit 4 through the antenna 34. If the RF signal transmitter 22 receives the "range off" message, it does not send out any RF signal transmission. The RF signal transmitter 22 continuously transmits the "cardiac arrest," "manual heart attack," "other emergency," "clasp reclosed," "wrist on," "wrist off," "wrist error," and "shock received" signals for approximately five seconds whenever these signals are appropriate. The RF signal transmitter 22 then stops transmitting and waits to receive another control message from the prioritization and output activation module 40. The RF signal transmitter 22 transmits the "low wrist battery," "clasp open," and "pulse okay" signals for approximately one-half of a second and continues to repeatedly transmit these RF messages once every 3 seconds until it receives another control message from the prioritization and output activation module 40. The RF signal transmitter 22 continuously transmits the "range on" signal until it receives another message from the prioritization and output activation module 40. All RF signals transmitted by a wrist unit's RF signal transmitter 22 are coded such that no wrist unit can activate a base unit not associated with it. However, multiple base units 4 can be made to be compatible with one wrist unit 2. Similarly, a single base unit 4 can be specially programmed to be compatible with multiple wrist units 2.

It will be recognized by those skilled in the art of wireless transmissions that a number of known schemes might be used to transmit the RF signals, including, for example, not only modulated carrier schemes such as FM or AM transmission but also various noncarrier transmission schemes. If a carrier is used, it will be generally desirable to transmit the carrier only intermittently when a message is to be transmitted to reduce power consumption in the wrist unit 2. Further, those skilled in the art will recognize that a variety of encoding, signal pulsing, or other schemes known for transmitting information messages over a communications link of a given bandwidth can be used to differentiate the various messages transmitted by the RF transmitter 22 so that RF signal decoder 46 can determine which signal was transmitted as will be explained later in more detail. Also, a variety of schemes are available for differentiating signals produced by different wrist units 2, such as using different transmitting frequencies for different wrist units or such as adding an identification component to the message coding. Any of the available schemes for transmitting all of this essential information may be selected in accordance with the principles of the present invention.

The audio signal device 24 produces a continuous sound (100% duty cycle) if it receives the "cardiac arrest" or "manual heart attack" message from the prioritization and output activation module 40. If it receives the "other emergency" message, the audio signal device 24 produces a non-continuous sound (50% duty cycle). The audio signal device 24 produces a non-continuous "bipping" sound (10% duty cycle) if it receives the "wrist error," "low wrist battery," or "clasp open" message. The audio signal device 24 makes a single "bip" sound if it receives the "wrist on" or "wrist off" message. The audio signal device 24 becomes silent if it receives the "range on," "range off," "clasp reclosed," "pulse okay," or "shock received" message. The audio signal device 24 continues to produce its sound (or remains silent) until it receives another message from the prioritization and output activation module 40.

The prioritization and output activation module 40 of the microcontroller 12 may operate using software developed according to the flowchart of FIG. 5. Those skilled in the art will recognize that the details of the software provided for microcontroller 12 will depend on the microcontroller 12 selected and the assignment and connection of the input devices to the ports of the microcontroller 12. In general, the prioritization and output activation module 40 can activate thirteen possible "functions" of the wrist unit 2, which generate the collective responses of the wrist unit 2's three output devices to signals sent by the prioritization and output activation module 40. In determining which function should be executed, the prioritization and output activation module 40 first checks for a condition that makes a response appropriate and then activates the output devices of the wrist unit 2 to perform the function if the condition is found. As shown at section 500 of the flowchart of FIG. 5, the prioritization and output activation unit 40 will scan these possible functions from highest to lowest priority (for PRIORITY=1 to 13 as shown in Table 1), and the first function found during this scan that is appropriate for execution, which will also be the highest priority function appropriate for execution, will cause an exit of the loop for execution of the function.

The scan continues in the loop of section 500 from highest to lowest priority and will be repeated until such time as a function is identified for execution.

In determining whether a function is appropriate for execution, the prioritization and output activation unit 40 first scans inputs relevant to the function as shown in block 504. Briefly, the primary inputs relevant to each message (and thus function) which were discussed previously in the specification are summarized again in Table 2:

TABLE 2

| MESSAGE | PRIMARY INPUT |
|---|---|
| shock received | defibrillation sensor 17 |
| wrist off | on/off button 26 and present operational state |
| wrist on | on/off button 26 and present operational state |
| manual heart attack | manual heart attack button 28 |
| other emergency | other emergency button 30 |
| cardiac arrest | timer module 38 |
| wrist error | diagnostic circuits 23 |
| clasp reclosed | clasp detector 19 and present clasp state |
| clasp open | clasp detector 19 and present clasp state |
| low wrist battery | low battery detector 21 and timer expiration |
| range off | range determ. feature button 32 and present operational state |
| range on | range determ. feature button 32 and present operational state |
| pulse okay | wrist unit in active state and timer module 38 |

The pulse okay and low wrist battery functions will be executed only when the wrist unit is active (turned on) and when a timer of, for example, three seconds in timer module 38 has expired indicating that three seconds have lapsed since the transmission of the last RF signal. This feature reduces the power requirements of the wrist unit 2 since, in normal operation, the pulse okay signal or low wrist battery signal (which also indicates that the pulse is okay) will be transmitted only every three seconds. The expiration of this timer, however, is the only requirement other than activation of the wrist unit 2 for transmission of the pulse okay signal. Thus, unless one of the higher priority signals, such as a cardiac arrest signal, is selected for execution prior to reaching the "pulse okay" function which is the last selectable function in the loop, the pulse okay function will be executed every three seconds.

The condition of the inputs determining whether each function should be executed, as shown in Table 2, is examined by prioritization and output activation unit 40 at block 506 in FIG. 5 to determine whether or not the function should be executed. When a function is to be executed, the prioritization and output activation unit 40 will perform the functions as shown in block 502 for that function, including the provision of data to a display advice, transmission of the appropriate RF signal, and transmission of any appropriate audio signal through the audio signal device 24. The thirteen possible functions of wrist unit 2, along with their priorities and the appropriate display, RF signal, and audio outputs to be executed for these functions, are summarized in Table 3:

TABLE 3

| PRIORITY | MESSAGE[1,2] | DISPLAY DEVICE | RF SIGNAL TRANSMITTER | AUDIO SIGNAL DEVICE |
|---|---|---|---|---|
| 1 | "shock received" | Cleared | "shock received" | Silent |
| 2 | "wrist off" | "OFF" | "wrist off" | 1 bip |
| 3 | "wrist on" | Cleared | "wrist on" | 1 bip |
| 4 | "manual heart attack" | "HEART" | "manual heart attack" | 100% duty cycle |
| 5 | "other emergency" | "OTHER" | "other emergency" | 50% duty cycle |
| 6 | "cardiac arrest" | "HEART" | "cardiac arrest" | 100% duty cycle |
| 7 | "wrist error" | "ERROR" | "wrist error" | 10% duty cycle |
| 8 | "clasp reclosed" | Cleared | "clasp reclosed" | Silent |
| 9 | "clasp open" | "CLASP" | "clasp open" | 10% duty cycle |
| 10 | "low wrist battery" | "BAT" | "low wrist battery" | 10% duty cycle |
| 11 | "range off" | Cleared | No RF transmission | Silent |
| 12 | "range on" | "RANGE" | "range on" | Silent |
| 13 | "pulse okay" | Cleared | "pulse okay" | Silent |

[1] The prioritization and output activation module 40's message to the wrist unit's output devices have the same name as the message that the prioritization and output activation module 40 receives from various sources in the wrist unit.
[2] The messages are arranged in order of decreasing priority.

Thus, the prioritization and output activation module 40 will first scan the defibrillation sensor input to see if the "shock received" message is appropriate since this message has PRIORITY=1. If this message is appropriate, as shown in Block 506, the prioritization and output activation module 40 will then exit the loop of section 500 and activate the output units to perform the functions corresponding to the "shock received" message (as shown in section 502). If this message is not appropriate based on checking of the condition of the relevant inputs, the loop of section 500 will continue with the next highest priority message until an appropriate message is found. In this manner, the first message found to be appropriate will necessarily be the highest priority message appropriate at the time. Thus, the "pulse okay" message and its corresponding function will only be appropriate if none of the other messages are appropriate.

The operation of the base unit 4 will now be described in detail with reference to FIG. 1. As FIG. 1 shows, the base unit 4 has an antenna/power cord 42 that both receives RF signals from the wrist unit 2 and serves as a means to access 120V AC power from a standard household power receptacle, which is the base unit 4's primary power source. (Even though the antenna is shown to be inside the power cord in this embodiment of the base unit 4, the antenna may instead be inside the base unit 4.) The base unit 4 is also provided with a telephone connector 43 which allows the base unit 4 to access the public switched telephone network by means of a standard RJ-11C connector. The base unit 4 has an on./off switch 52 and a siren/annunciator deactivator button 54, the operations of which are explained in more detail below.

The base unit 4 also contains an external display panel 56 which may be a light emitting diode (LED) display, a CPR instructions player 64 which is preferably a removable and portable digital message player that plays concise CPR instructions when one of its buttons is pressed, an internal compartment 66 which opens up when the compartment button 67 is pressed, a power light 68 which is lit when the base unit 4 is activated, a medical card slot 69 which houses a removable medical information card providing information about the user of the system, and a volume control knob 70 which adjusts the volume of the base unit's audio signal devices (which are described below).

The CPR instructions player 64 can be removed from the base unit 4 by a caregiver in case of a cardiac emergency. This message player will preferably have brief written instructions associated therewith such as by printing on the case of CPR instructions player 64, but will also have simple, non-language-specific illustrations of proper positions for cardiopulmonary resuscitation (CPR) or other appropriate emergency medical procedures associated therewith, and will function to selectively play a pre-recorded instructional message that describes in real time how to implement CPR. While the instructions player 64 will be described in the present, preferred embodiment as providing CPR instructions, instructions player 64 may also provide instructions for performing other emergency medical procedures, such as the Heimlich maneuver.

Figure 6:
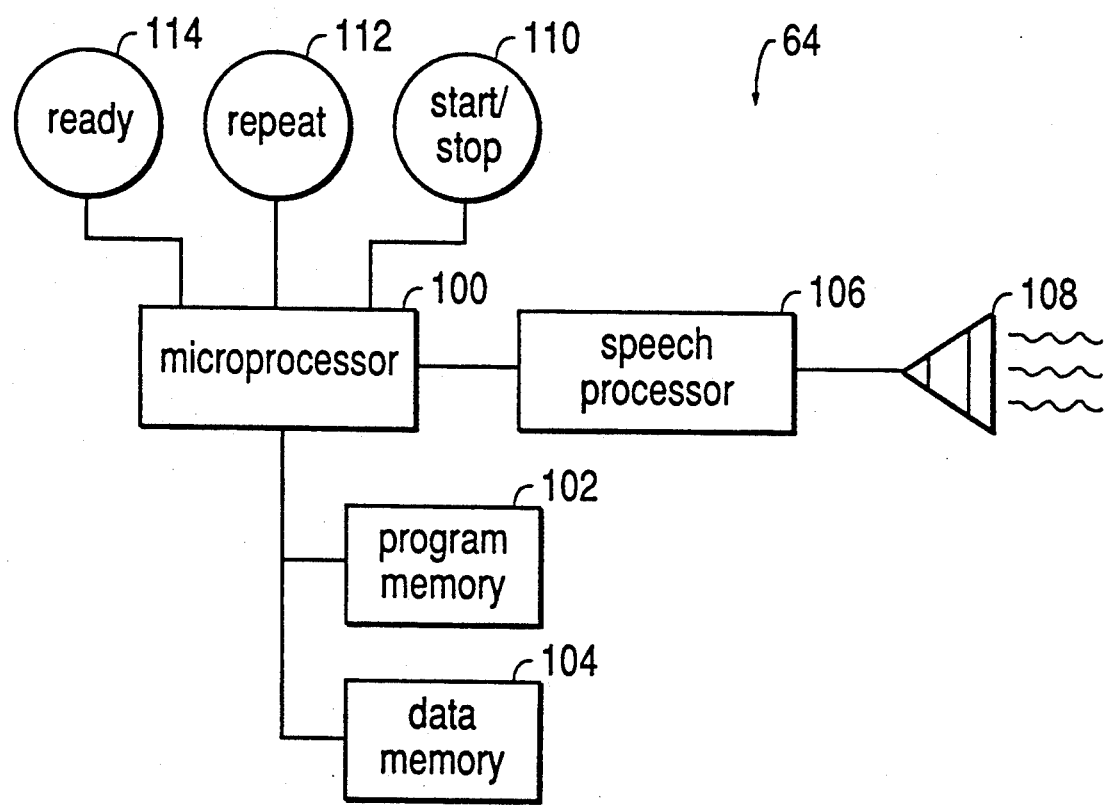
FIG. 6 is a block-schematic diagram of the instructions player of the present invention.

The instructions player 64 is preferably designed according to the diagram of FIG. 6, with no moving parts, including a microprocessor 100 connected to a program memory 102, data memory 104, and a speech processor 106 capable of generating a synthesized voice through a speaker/amplifier 108 connected to the speech processor 106. The program memory 102 will contain a simple program which causes the microprocessor to transfer in a desired order specified data from the data memory 104 to the speech processor 106, directing that the speech processor 106 generate certain synthesized voice sounds. The sound of the synthesized voice selected should be both calm and authoritative since the instructions player 64 is designed for the use of lay persons who are dealing with an unfamiliar emergency and who are likely to be frightened or agitated. The instructions player 64 is provided with batteries for powering its circuits (not shown). The batteries are preferably maintained in a charged state by the base unit 4 when the instructions player 64 is not being used.

The instructions player 64 may have a plurality of control means in the form of switching devices connected as inputs to ports of the microprocessor 100, such as a start/stop button 110, repeat button 112, and ready button 114. These control buttons will be used by the caregiver to control the broadcast of the medical procedure instructions through speaker 108, which may be an amplified speaker. The start/stop button 110 will activate and deactivate the instructional broadcast. The repeat button 112 will cause the instructions player 64 to repeat the most recent instruction block and can be pressed by the caregiver to indicate that the instruction just given was not completely understood and that repeating of the instructions is desired. The ready button 114 is pressed by the caregiver to indicate that the instructions just received were understood or that they were carried out, as appropriate, thus ensuring that the system interacts appropriately with the caregiver and adapts to the caregiver's speed of execution. Additional control buttons for selection of different programs could be provided if the instructions player 64 is provided with multiple instructional programs for performing a number of medical procedures. The microprocessor 100 may also be programmed so that certain portions of the instructions are automatically repeated at intervals until the ready button 114 is pressed. This feature will be particularly useful in giving CPR positioning instructions.

Figure 7:
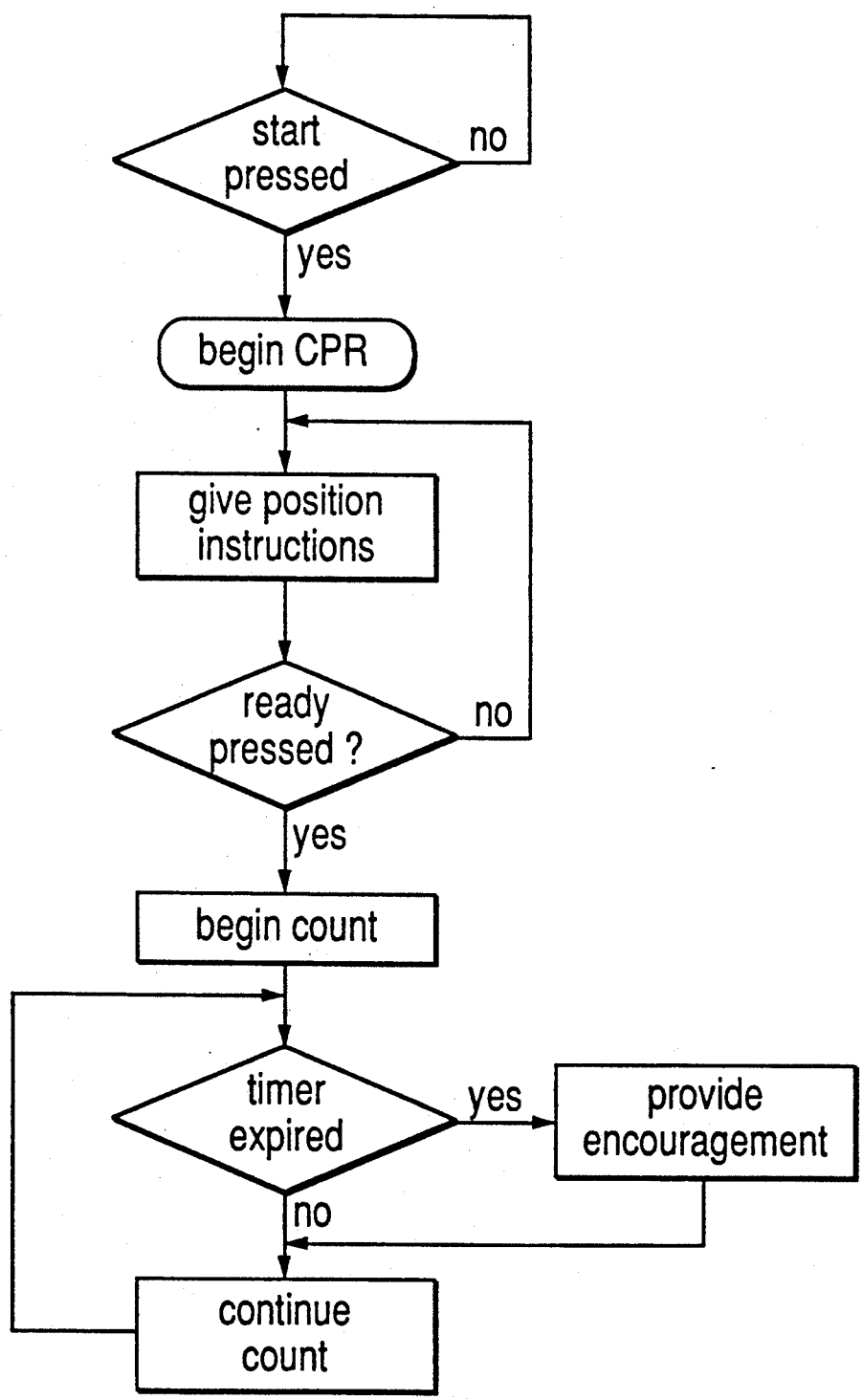
FIG. 7 is a flowchart showing the operation of the instructions player of the present invention.

In the present example, when the instructions player 64 gives CPR instructions, the program of instructions player 64 will operate generally according to the procedure depicted in the flowchart of FIG. 7. When the start button 110 is pressed, the instructions player 64 will broadcast verbal instructions. These instructions may first include positioning instructions, or directions for positioning the person whose heart has stopped for CPR and also for preparing the chest area and airway, locating the proper point for the application of pressure, and assuming the proper stance and hand position for chest compressions. The instructions will preferably refer to the positioning illustrations and instructions printed on the outer case of instructions player 64. It is preferred that the output of the position instructions be controlled with the repeat and ready buttons operating as described previously so that the caregiver can indicate at each step his or her readiness for the next instruction. For example, the instructions player 64 might broadcast "Roll the patient flat onto his or her back and press READY", repeating this message every few seconds until the ready button 114 is pressed. Only then would the next instruction, which might be, for example, "support the patient's head and tilt it gently back so that his or her chin is pointing toward the ceiling" be given.

When the caregiver has prepared the patient and has assumed the proper stance and hand position, the program may provide a real time count or rhythm for CPR chest compressions and breathing by synthesizing the word "press!", part of a numeric counting series such as one of the numbers 1–5, or a similar command at the required intervals, and also by giving directions as to the timing of breathing. For example, the sequence could be "1-2-3-4-5-breathe" or "press-press-press-press-press-breathe." Another timer or counter may also be provided so that, at periodic intervals, further instructions, reminders, or encouragement may be given, such as "You're doing fine," "You should press hard enough to move the surface of the chest down about an inch," "You've been working for three minutes. Just keep going a little longer—the ambulance should be here soon," and periodically, "Stop now and check to see if the patient has started breathing on his own."This rhythmic portion of the instructions given by instructions player 64 will be continued until such time as the instructions player 64 is turned off, generally when the patient has been revived or upon the arrival of the paramedics.

Of course, the preferred sequence of instructions given herein assumes that a cardiac arrest has already been positively detected by the system of the present invention. If the instructions player 64 were to be used in the absence of such a determination, preliminary instructions designed to help the caregiver determine whether or not CPR administration is necessary, and an instruction to call paramedics, would be appropriate and desirable.

Also, although it is much preferred that the instructions player 64 be removable from the base unit 4 so that it can be taken directly to the location of a user in need of emergency care, the instructions player 64 could also be made a part of the base unit 4 and provided with a larger speaker that could be heard for a considerable distance. In addition, the instructions player 64 could be a magnetic tape player which would merely replay analog recorded instructions when activated, although a tape recording would lack certain utility provided by the preferred system. Further, although the instructions player 64 has been described in terms of CPR instructions, the instructions player 64 might be provided with instructions for any number of other procedures, such as the Heimlich maneuver, either alone or in addition to CPR instructions. If the unit is designed to give instructions for multiple procedures, selection means would be provided for selecting the desired set of instructions i.e., instructions for CPR, Heimlich maneuver, etc.

The instructions player 64 of the present invention permits relatively untrained persons to give lifesaving CPR, but would also be a useful aid to trained personnel in that it provides a steady, accurate rhythm for compressions and breathing to ensure high-quality CPR. In addition, even those who have been trained in CPR may not have had very recent training and thus an instant refresher course as provided by the instructions player 64 will be useful. Also, the preparatory instructions provided ensure that no preparatory step is omitted. Thus, even those who have been regularly trained in CPR will appreciate the guidance and aid to memory provided by the instructions player 64.

While the instructions player 64 would be useful alone, it serves a particularly important synergistic function when associated with the overall system of the present invention. An important object of the system of the present invention is to save the life of a person experiencing cardiac arrest. Toward that end, as will be seen, the system is designed to bring the victim the most prompt total emergency assistance possible by providing alarms at three separate locations: the specific location of the user (by audio signal device 24 of wrist unit 2), the larger immediate area where the user is, such as throughout the user's house (by signal devices of base unit 4) and in the geographic region where the user is located (by the telephone auto dialer 62 of base unit 4).

Each of these alarms has a specific purpose and the three alarms work together to bring emergency care to the victim in the shortest possible time. The alarm of wrist unit 2 informs the user personally that something is wrong. If the user is still conscious, the user can take steps to minimize health risk, such as by sitting down, taking medication if advised, and seeking medical assistance. The alarm of wrist unit 2 also allows caregivers to "home in" on the sound to locate the victim when, as in a cardiac arrest, the victim is unconscious. Further, in the unlikely event of a false alarm, the user will immediately know of the false alarm because of the alarm of wrist unit 2 and can take steps to silence the alarm. The structure- or area-wide alarm sounded by the signal devices of base unit 4 alerts potential caregivers in the immediate area, such as a spouse in another part of the house, so that immediate assistance can be rendered by these persons already on the scene. Finally, in the overall scheme, the auto dialer 62 of base unit 4 alerts community emergency medical services so that paramedics will be dispatched immediately.

Even though the present invention thus insures that the paramedics will be notified of a cardiac arrest very soon after it occurs, the victim's chances of surviving improve dramatically if he or she receives CPR rapidly. Even if an ambulance is called right away, in some parts of the country an ambulance may not arrive in time to save the patient if CPR is not administered during the ambulance's travel time. The importance of the instructions player 64 in the overall scheme of the present invention is thus apparent. While the persons originally present in the victim's immediate area might not otherwise be able to render effective assistance, the combination of the alarm which alerts them to the problem and the instructions player 64 which provides them with a means for rendering effective first aid allows even untrained persons in the immediate area to provide lifesaving care. The combination of localized alarms and caregiving instructions provided by the present invention thus provides a complete system which immediately diagnoses a cardiac arrest and ensures the swiftest and most effective emergency treatment possible for a cardiac arrest outside of a hospital cardiac unit setting.

The medical card slot 69 of base unit 4 houses a medical summary card which may contain critical medical information about the user of the monitoring and warning system. Such information might include medical and personal history, drug allergies, medications being taken, insurance information, and other information useful to an emergency caregiver.

Figure 8:
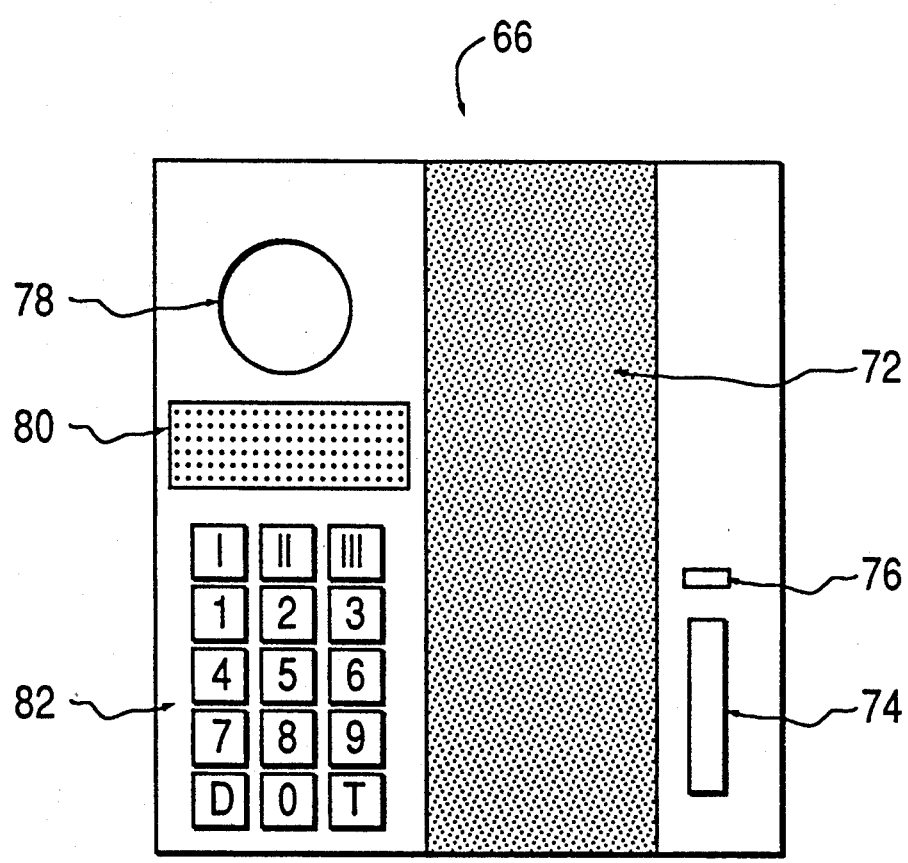
FIG. 8 is an illustration showing the internal compartment of the base unit of the present invention.

Additional features and components of the base unit 4 will now be described with reference to FIG. 8, which is a top view of the inside of the internal compartment 66 of the base unit 4. The internal compartment 66 has a wrist unit storage area 72 where the wrist unit 2 may be stored and/or charged, a wrist unit battery recharger 74 which continuously keeps an extra battery for the wrist unit 2 charged and can recharge a depleted wrist unit battery, and a battery charge indicator 76 which may be an LED that indicates whether the extra wrist unit battery in the battery recharger 74 is fully charged. The internal compartment 66 also contains the programming controls for the base unit 4. These controls include a microphone 78, a keypad display unit 80 which may be an LED readout, and a keypad 82. A user of the system can use the microphone 78 to record messages for the base unit's annunciator 60 and auto dialer 62 (both of which are described in detail below) and the keypad 82 to input telephone numbers and other information. The keypad display unit 80 displays visual instructions for using the microphone 78 and the keypad 82.

Although the basic base unit 4 accommodates one wrist unit 2, special base units 4 with multiple wrist unit storage areas 72, wrist unit battery rechargers 74, and battery charge indicators 76 can also be constructed for group living or work situations. These base units 4 will be made compatible with multiple wrist units 2 but the RF transmissions of each wrist unit 2 will be individually coded so that the base unit 4 can identify the originating wrist unit 2. Thus, the base unit 4 can independently determine the status of each wrist unit 2 and can take individualized appropriate action when a trouble signal is received from a wrist unit. For example, there may be different telephone numbers to be called or announcements to be made depending on the identity of the user wearing a particular wrist unit. In cases where wrist units 2 with significant RF transmitter range are provided, it may be desirable to code these transmissions for identification of the specific wrist unit 2 to prevent a person's wrist unit 2 from inadvertently activating a neighbor's base unit. In this way, a wrist unit 2 can be made to activate only a base unit 4 with which it is associated. Any of numerous methods known in the art for encoding transmissions for these purposes could be used. When coding schemes are used, the base unit 4 will be provided with a selection circuit for selecting, using the base unit keypad or some switching mechanism, the codes of wrist units 2 that the base unit 4 should respond to. There will also be provided a detection circuit for identifying the codes in incoming transmissions and comparing them to the selected codes. When the incoming code is not one which the base unit 4 has been programmed to respond to, the base unit 4 will not process the incoming signal further; in other words, the base unit 4 will not operate in the normal manner to respond to a signal of a non-associated wrist unit 2.

Figure 9:
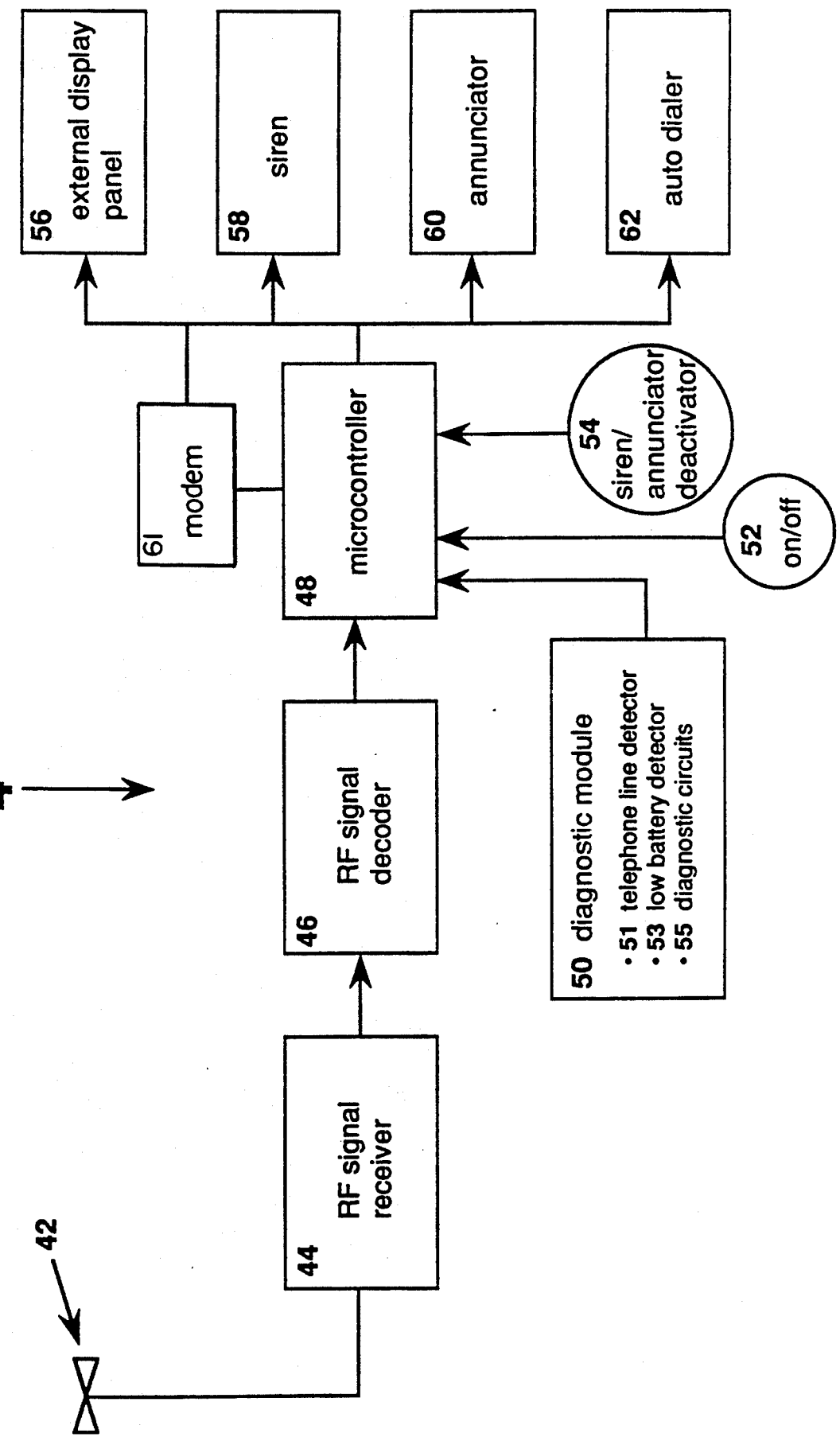
FIG. 9 is a block-schematic diagram of the base unit of the present invention.

FIG. 9 shows the components of the base unit 4 in block circuit form. Besides the antenna/power cord 42, on/off switch 52, siren/annunciator deactivator button 54, and external display panel 56, the base unit 4 contains an RF signal receiver 44, an RF signal decoder 46, a microcontroller 48 (which receives messages from various sources and sends out messages which activate the base unit's output devices), a diagnostic module 50 (which monitors the operation of the base unit and indicates malfunctions), two audio signal devices—a siren 58 which can make several different sounds and an annunciator 60 which broadcasts prerecorded verbal messages—and an auto dialer 62 which is connected to the public switched telephone network and calls preprogrammed telephone numbers to deliver prerecorded verbal messages over the telephone line. While in most cases the auto dialer 62 will be connected to the public switched telephone network by means of wires, the auto dialer 62 could also be connected to a cellular radiotelephone network or other available communications network.

The base unit's microcontroller 48 may have associated with it or otherwise include, in a preferred embodiment, a system memory which stores a record of each message that the microcontroller 48 receives and sends out. The microcontroller 48 may also store at the same time data from an internal clock to identify when the records were stored. The base unit 4 will be programmed to selectively transfer these records over the public switched telephone network by means of a modem 61 connected to the microcontroller 48. The modem 61 can be connected to a remote computer for data exchange therewith by means of the autodialer 62. Preferably, such records will be transferred automatically on a periodic basis to a central mainframe computer, which can be programmed to generate any desired reports on patient heart function and system function and use for transmission to the user's doctor or other authorized parties.

Finally, the base unit 4 has a back-up battery which provides enough power to ensure normal functioning of the base unit 4 for at least twelve hours if the base unit's primary power source is interrupted. This back-up battery is kept constantly recharged by the base unit's primary power source.

As shown in FIG. 9, the antenna/power cord 42 is connected to the RF signal receiver 44, which is connected to the RF signal decoder 46, which in turn is connected as an input to the microcontroller 48. The diagnostic module 50, on/off switch 52, and siren/annunciator deactivator button 54 are operably connected as inputs to the microcontroller 48. The external display panel 56, siren 58, annunciator 60, and auto dialer 62 are operably connected as output devices of the microcontroller 48. The modem 61 is connected to the microcontroller 48 and also to a telephone line associated with the auto dialer 62.

The base unit 4 receives RF signals from the wrist unit 2 through its antenna/power cord 42 and RF signal receiver 44. These RF messages are decoded by the RF signal decoder 46, and the decoded message from these signals is sent to the microcontroller 48. Thus, the base unit's microcontroller 48 can receive any of the following 12 messages from the wrist unit 2: "shock received," "wrist off," "wrist on," "manual heart attack," "other emergency," "cardiac arrest," "wrist error," "clasp reclosed," "clasp open," "low wrist battery," "range on," and "pulse okay."

As shown in FIGS. 1 and 9, the on/off switch 52 and the siren/annunciator deactivator button 54 are used to control some functions of the base unit 4. When the on/off switch 52 is flipped to the "on" position, it sends the "base on" message to the microcontroller 48 to activate the base unit 4. When the on/off switch 52 is flipped to the "off" position, it sends the "base off" message to the microcontroller 48 to totally deactivate the base unit 4. When the siren/annunciator deactivator button 54 is activated, it sends the "siren/annunciator off" message to the microcontroller 48 to indicate that the user of the system wishes to silence the siren 58 or the annunciator 60.

As shown in FIG. 9, the base unit's microcontroller 48 also receives messages from the diagnostic module 50. The diagnostic module 50 may be implemented using discrete logic components, using an independent microcontroller, using the microcontroller 48, or using a combination of discrete components and the microcontroller 48. The diagnostic module 50 may include a telephone line detector 51, a low battery detector 53, and other diagnostic circuits 56. The telephone line detector 51 sends the "telephone error" message to the microcontroller 48 if the telephone line to which the base unit 4 is connected is malfunctioning. The diagnostic module 50's low battery detector 53 sends the "low base battery" message to the microcontroller 48 if the base unit's back-up battery falls below a specified percentage of maximum charge when this battery is powering the base unit 4. As in the wrist unit 2, the diagnostic module 50's additional independent internal diagnostic circuits 55 diagnose malfunctions in other components of the base unit 4. When these diagnostic circuits 55 detect malfunctions, the "base error" message is sent to the microcontroller 48.

If the microcontroller 48 simultaneously receives a message that originated in the base unit 4 and a message from the wrist unit 2, the microcontroller 48 considers any message from t wrist unit 2 to be of higher priority than a base unit message, with the exception of the "base off" and "base on" messages, which always have the highest priority. Therefore, the microcontroller 48 prioritizes incoming messages as is shown in Table 4:

TABLE 4

| | |
|---|---|
| priority one | "base off" |
| priority two | "base on" |
| priority three | "shock received" |
| priority four | "wrist off" |
| priority five | "wrist on" |
| priority six | "manual heart attack" |
| priority seven | "other emergency" |
| priority eight | "cardiac arrest" |
| priority nine | "wrist error" |
| priority ten | "clasp reclosed" |
| priority eleven | "clasp open" |

TABLE 4-continued

| | |
|---|---|
| priority twelve | "low wrist battery" |
| priority thirteen | "range off" |
| priority fourteen | "range on" |
| priority fifteen | "pulse okay" |
| priority sixteen | "base error" |
| priority seventeen | "siren/annunciator off" |
| priority eighteen | "telephone error" |
| priority nineteen | "low base battery" |

When the microcontroller 48 receives any message, it activates the base unit's output devices—the external display panel 56, siren 58, annunciator 60, and autodialer 62—by sending appropriate signals to these devices based on the conditions sensed, operating in a manner similar to that described previously for the wrist unit 2. If it simultaneously receives more then one message, the microcontroller 48 sends the highest priority message to the output devices.

Usually the microcontroller 48 sends a message to the output devices as soon as it receives the message, but the microcontroller 48 delays sending the "manual heart attack," "other emergency," "cardiac arrest," "wrist error," and "clasp open" messages to the output devices for 10 seconds after it receives these messages. This delay helps reduce false alarms since it provides time for the user to cancel the alarm. The microcontroller 48 waits 1 hour after receiving the "low wrist battery" message before sending it to the base unit's output devices. The base unit 4 also incorporates a failsafe system which generates an alarm if it does not receive an RF signal from the wrist unit 2 for a defined time period. In the preferred embodiment, if the microcontroller 48 does not receive any message from the wrist unit 2 for 15 consecutive seconds, it generates and sends the "out of range" message to the output devices. In general, this delay may be chosen to be some defined multiple of the time period between RF signals from the wrist unit 2 in normal operation. In the example herein, the wrist unit 2 should send a "pulse okay" RF signal every three seconds in normal operation, and the failsafe alarm is programmed to operate after RF signals and their corresponding messages are absent for five consecutive message periods.

The responses of the output devices of the base unit 4 to each possible status message from the microcontroller 48 will now be described in detail. The external display panel 56 is cleared if it receives the "base off," "base on," "shock received," "wrist off," "wrist on," "clasp reclosed," "pulse okay," or "siren/annunciator off" message from the microcontroller 48. The external display panel 56 displays "HEART ATTACK" if it receives the "manual heart attack" or "cardiac arrest" message, "OTHER EMERGENCY" if it receives the "other emergency" message, "WRIST ERROR" if it receives the "wrist error" message, "CLASP OPEN" if it receives the "clasp open" message, "LOW WRIST BATTERY" if it receives the "low wrist battery" message, "TESTING RANGE" if it receives the "range on" message, "OUT OF RANGE" if it receives the "out of range" message, "BASE ERROR" if it receives the "base error" message, "TELEPHONE ERROR" if it receives the "telephone error" message, and "LOW BASE BATTERY" if it receives the "low base battery" message. The external display panel 56 maintains its display (or remains cleared) until it receives another message from the microcontroller 48.

The siren 58 is silent if it receives the "base off," "base on," "shock received," "clasp reclosed," "pulse okay," or "siren/annunciator off" message from the microcontroller 48. The siren 58 makes a single chime if it receives the "wrist off" or "wrist on" message. The siren 58 produces a continuous sound (100% duty cycle) for 15 seconds if it receives the "manual heart attack" or "cardiac arrest" message and a non-continuous sound (50% duty cycle) for 15 seconds if it receives the "other emergency" message. The siren 58 produces a non-continuous "bipping" sound (10% duty cycle) if it receives the "wrist error," "clasp open," "low wrist battery," "out of range," "base error," "telephone error," or "low base battery" message and continues to produce this 10% duty cycle "bipping" sound until it receives another message from the microcontroller 48. For as long as it receives the "range on" message, the siren 58 produces a continuous sound (100% duty cycle) which varies in pitch and volume according to the strength of the RF "range on" message that the base unit 4 receives from the wrist unit's RF signal transmitter 22. This varying sound enables the wearer of the wrist unit 2 to determine the wrist unit's range of RF transmission to the base unit 4 and the location of any areas within this range where RF transmission from the wrist unit 2 to the base unit 4 is inhibited.

The annunciator 60 and the auto dialer 62 remain silent if they receive the "base off," "base on," "shock received," "wrist off," "wrist on," "wrist error," "clasp reclosed," "clasp open," "low wrist battery," "range on," "pulse okay," "out of range," "base error," "siren/annunciator off," "telephone error," or "low base battery" message from the microcontroller 48. The annunciator 60 broadcasts a brief verbal message once every 15 seconds which alerts people in the home of a heart attack if it receives the "manual heart attack" or "cardiac arrest" message. If it receives the "other emergency" message, the annunciator 60 broadcasts a brief prerecorded verbal message once every 15 seconds which alerts people in the home to a non-cardiac emergency. The annunciator 60 continues to broadcast its verbal message until it receives another message from the microcontroller 48. The auto dialer 62 calls a sequence of pre-programmed telephone numbers and delivers the corresponding appropriate prerecorded message when each of these calls is answered if it receives the "manual heart attack" or "cardiac arrest" message. The auto dialer 62 may call a different sequence of numbers and deliver different messages if it receives the "other emergency" message depending on how the user programmed the auto dialer 62. The auto dialer 62 continues its calling sequence until it receives another message from the microcontroller 48.

The base unit 4 may be provided with control outputs (not shown) such as switchable 120V AC power outlets for activating external devices during an alarm condition such as a cardiac arrest situation. Such control outputs might be used to unlock or open doors, turn on lights, or sound additional external alarms, among other uses.

The procedures followed by the microcontroller 48 of base unit 4 and the base unit's output devices are summarized in Table 5:

TABLE 5

| MESSAGE[1,2] | EXTERNAL DISPLAY PANEL | SIREN | ANNUNCIATOR & AUTO DIALER |
|---|---|---|---|
| "base off" | Cleared | Silent | Silent |
| "base on" | Cleared | Silent | Silent |
| "shock received" | Cleared | Silent | Silent |
| "wrist off" | Cleared | 1 chime | Silent |
| "wrist on" | Cleared | 1 chime | Silent |
| "manual heart attack" | "HEART ATTACK" | 100% duty cycle | Heart sequence[3] |
| "other emergency" | "OTHER EMERGENCY" | 50% duty cycle | Other sequence[4] |
| "cardiac arrest" | "HEART ATTACK" | 100% duty cycle | Heart sequence |
| "wrist error" | "WRIST ERROR" | 10% duty cycle | Silent |
| "clasp reclosed" | Cleared | Silent | Silent |
| "clasp open" | "CLASP OPEN" | 10% duty cycle | Silent |
| "low wrist battery" | "LOW WRIST BATTERY" | 10% duty cycle | Silent |
| "range on" | "TESTING RANGE" | 100% duty cycle[5] | Silent |
| "pulse okay" | Cleared | Silent | Silent |
| "out of range" | "OUT OF RANGE" | 10% duty cycle | Silent |
| "base error" | "BASE ERROR" | 10% duty cycle | Silent |
| "siren/annunciator off" | Cleared | Silent | Silent |
| "telephone error" | "TELEPHPNE ERROR" | 10% duty cycle | Silent |
| "low base battery" | "LOW BASE BATTERY" | 10% duty cycle | Silent |

[1] The microcontroller 48's messages to the base unit's output devices have the same name as the messages that the microcontroller 48 receives from various sources.
[2] The messages are arranged in order of decreasing priority.
[3] The annunciator broadcasts a verbal message alerting people in the home of a heart attack and the auto dialer calls telephone numbers and alerts other parties of a heart attack.
[4] The annunciator broadcasts a verbal message alerting people in the home of a non-cardiac emergency and the auto dialer calls telephone numbers and alerts other parties of a non-cardiac emergency.
[5] This continuous sound varies in pitch and volume according to the strength of the wrist unit's RF transmissions.

The microcontroller 48 of base unit 4 will implement a program which performs the functions described in Table 5 when the messages shown are received, and which also operates according to the description contained herein.

STATEMENT OF INDUSTRIAL APPLICABILITY

The system of the present invention will find its primary application in the monitoring of people who are at high risk of having a heart attack in their home or office where it will automatically summon aid in case of a cardiac arrest and will be used to manually summon aid in other cardiac and non-cardiac emergency situations. However, the system may also be used in hospitals, clinics, nursing homes, and retirement communities. It may also be used by military personnel while they are performing exercises or are engaged in combat.

Although the description of this invention has been given with reference to a particular embodiment, it is not to be construed in a limiting sense. Many variations and modifications of the invention will now occur to those skilled in the art without departing from the spirit and scope thereof, which is defined by the appended claims.

We claim:

1. A system for monitoring the physiological condition of a user and alerting people to a user physiological condition problem, comprising:

monitor means for monitoring physiological condition of the user and transmitting signals indicative of said physiological condition, said monitor means worn on the body of said user and portable, said monitor means including:

sensing means selectively actuated by said monitor means for sensing the physiological condition of said user; and transmitting means actuated by said monitor means for transmitting at least one wireless signal indicative of the second physiological condition of said user;

base unit means for receiving said wireless signals from said transmitting means associated with said monitor means and analyzing said signals to determine the existence of said user physiological condition problem, said base unit means physically separate from said monitor means;

message delivery means adapted for connection to a communications network and associated with and actuated by said base unit means for automatically delivering at least one message indicative of said user physiological condition problem on said communications network for summoning emergency assistance when said wireless signals indicative said user physiological condition problem.

2. The system of claim 1 wherein the message delivery means comprises a telephone network connection and delivers at least one message on said connected telephone network in response to said user physiological condition problem.

3. The system of claim 2 wherein the base unit means includes sound producing means for automatically delivering at least one audible message to at least one location remote from the base unit means via the message delivery means through said communications network.

4. The system of claim 1 wherein said monitor means determines the existence of a user physiological condition problem and transmits a signal specifying said user physiological condition to the base unit means.

5. A system for monitoring the heart condition of a user and alerting people to a user heart condition problem, comprising:

monitor means for monitoring heart function of a user and transmitting signals indicative of said heart function, said monitor means worn on the body of said user and portable, said monitor means comprising sensing means actuated by said monitor means for sensing the heart condition of said user and transmitting means actuated by said monitor means for transmitting at least one wireless signal indicative of the sensed heart condition of said user;

base unit means for receiving said wireless signal from said transmitting means and selectively providing an indication output in response to said wireless signal, said base unit means physically separate from said monitor means; and message delivery means adapted for connection to a communications network and associated with and actuated by said base unit means for automatically delivering at least one message indicative of said user heart condition problem on said communications network when said wireless signals indicative said user heart condition problem.

6. The system of claim 5 wherein the message delivery means comprises a telephone network connection and delivers at least one message on said connected telephone network in response to said user heart condition problem.

7. The system of claim 6 wherein the base unit means includes sound producing means for automatically delivering at least one audible message to at least one location remote from the base unit means via the message delivery means through said telephone network.

8. The system of claim 5 wherein said monitor means determines the existence of a user heart condition problem and transmits a signal specifying said user heart condition problem to the base unit means.

9. A system for monitoring the heart condition of a user and alerting people to a user heart condition problem, comprising:

monitor means for monitoring heart function of a user and transmitting signals indicative of said heart function, said monitor means worn on the arm of said user and portable and compact, said monitor means including sensing means actuated by said monitor means for sensing the heart condition of said user and transmitting means actuated by said monitor means for transmitting at least one radio frequency signal indicative of the sensed heart condition of said user;

base unit means physically separate from said monitor means for receiving said radio frequency signals from said monitor means and for selectively generating an output indication in responses to the detection of said user heart condition problem; and message delivery means adapted for connection to a telephone network and associated with and actuated by said base unit means for automatically delivering at least one message indicative of a user heart condition problem on a telephone network for summoning emergency assistance when said radio frequency signals indicate said user heart condition problems.

10. The system of claim 9 wherein the monitor means includes determining means for determining the current heart condition of the user of said monitor means from the information provided by the sensing means and wherein said determining means causes the transmitting means to transmit at least one radio frequency signal indicative of a user heart condition problem if said determining means determines any said user heart condition problem.

11. The system of claim 10 wherein the determining means determines that the user has a heart condition problem only if the sensing means detects a user heart condition abnormality continuously for a specified time period.

12. The system of claim 11 wherein the specified time period is the time interval required for the sensing means to monitor the heart condition of the user at least three consecutive times.

13. The system of claim 10 wherein the determining means determines that the user has a heart condition problem only if the sensing means detects that said user is having a cardiac arrest.

14. The system of claim 13 wherein the determining means determines that the user is having a cardiac arrest only if the sensing means detects a user cardiac arrest continuously for a specified time period.

15. The system of claim 14 wherein the specified time period is the time interval required for the sensing means to monitor the heart condition of the user at least three consecutive times.

16. The system of claim 9 wherein the monitor means transmits radio frequency signals indicative of all of the heart condition information of the user provided by the sensing means when said sensing means is monitoring the heart condition of said user.

17. The system of claim 16 wherein the monitor means transmits radio frequency signals containing information on more than one monitoring attempt by the sensing means, said radio frequency signals being transmitted less frequently than said sensing means monitors the heart condition of the user.

18. The system of claim 17 wherein the monitor means transmits radio frequency signals indicative of each instantaneous heart beat rate of the user that is detected by the sensing means.

19. The system of claim 16 wherein the monitor means transmits radio frequency signals indicative of one of a normal user heart condition and an abnormal user heart condition.

20. The system of claim 19 wherein the only abnormal user heart condition indicated by the monitor means is a cardiac arrest.

21. The system of claim 9 wherein the monitor means transmits radio frequency signals indicative of one of a normal user heart condition and an abnormal user heart condition.

22. The system of claim 21 wherein the only abnormal user heart condition indicated by the monitor means is a cardiac arrest.

23. The system of claim 9 wherein the monitor means transmits at least one radio frequency signal indicative of the operations of said monitor means and wherein said monitor means continuously transmits at least some of the radio frequency signals indicative of at least one of the heart condition of the user and the operations of said monitor means to increase the likelihood that said radio frequency signals will be received by the base unit means.

24. The system of claim 9 wherein the monitor means includes powering means for providing power to said monitor means, said powering means including at least one rechargeable battery.

25. The system of claim 24 wherein the base unit means includes charging means for charging the powering means.

26. The system of claim 9 wherein the monitor means includes diagnostic means for determining an operational problem in said monitor means and wherein said diagnostic means causes the transmitting means to transmit at least one radio frequency signal indicative of any said operational problem.

27. The system of claim 9 wherein the base unit means includes diagnostic means for determining a problem with the operation of said base unit means.

28. The system of claim 27 wherein the diagnostic means includes telephone line surveillance means for determining an operational problem in the telephone line to which the base unit means is connected.

29. The system of claim 9 wherein the message delivery means includes sound producing means for delivering at least one audible message to at least one location remote from the base unit means through said telephone network.

30. The system of claim 9 wherein the monitor means includes attachment means for securing said monitor means to the arm of the user and also includes attachment sensing means for determining the attachment status of said attachment means with respect to said arm of said user and signalling said attachment status to said monitor means.

31. The system of claim 30 wherein the attachment means surrounds a portion of the arm of the user and is selectively separable to form two separated ends thereby permitting attachment and removal of the monitor means relative to said arm and wherein the attachment sensing means comprises a device responsive to the connection of the two ends of said attachment means.

32. The system of claim 30 wherein the monitor means has at least two operating modes, operating in a first operating mode when the attachment sensing means determines a secured attachment status of the attachment means and operating in a second operating mode when said attachment sensing means determines an unsecured attachment status of said attachment means.

33. The system of claim 9 wherein the monitor means has at least two operating modes whereby said monitor means performs all of its operations in a first operating mode and suspends some of its operations in a second operating mode.

34. The system of claim 29 wherein the monitor means includes notifying means for providing an indication at the immediate location of said monitor means when said monitor means determines that the user has a specified heart condition problem and said monitor means is operating in a particular predetermined operating status.

35. The system of claim 34 wherein the notifying means includes sound producing means to broadcast at least one audible sound.

36. The system of claim 34 wherein the notifying means includes visual display means to display at least one visible message.

37. The system of claim 34 wherein the notifying means includes sound producing means to broadcast at least one audible sound visual display means to display at least one visible message.

38. The system of claim 37 wherein the visual display means can display the time of day.

39. The system of claim 34 wherein the monitor means includes attachment means for securing said monitor means to the arm of the user and also includes attachment sensing means for determining the attachment status of said attachment means with respect to said arm of said user.

40. The system of claim 39 wherein the monitor means has at least two operating modes, operating in a first operating mode when the attachment sensing means determines a secured attachment status of the attachment means and operating in a second operating mode when said attachment sensing means determines an unsecured attachment status of said attachment means, and whereby said attachment sensing means causes the notifying means to indicate said unsecured attachment status.

41. The system of claim 39 wherein said attachment sensing means is connected to said transmitting means and said transmitting means further operates to signal said attachment status to said monitor means.

42. The system of claim 34 wherein the monitor means includes diagnostic means for determining an operational problem in said monitor means and wherein said diagnostic means causes the transmitting means to transmit at least one radio frequency signal indicative of any said operational problem and causes the notifying means to indicate any said operational problem.

43. The system of claim 42 wherein the diagnostic means includes charge determining means for determining the charge status of any batteries powering the monitoring means.

44. The system of claim 9 wherein the base unit means includes indicating means for providing an indication in a proximate surrounding area of said base unit means when the radio frequency signals transmitted by the monitor means are one of unreceived by said base unit means, and received by said base unit means and indicative of a specified heart condition of the user.

45. The system of claim 44 wherein the indicating means includes sound producing means to broadcast at least one audible sound.

46. The system of claim 44 wherein the indicating means includes visual display means to display at least one visible message.

47. The system of claim 44 wherein the indicating means includes sound producing means to broadcast at least one audible sound and visual display means to display at least one visible message.

48. The system of claim 47 wherein the sound producing means broadcasts verbal messages.

49. The system of claim 48 wherein the base unit means includes repository means for storing digital data representative of at least one verbal message and converting means for converting said digital data to an analog form suitable for verbal broadcast.

50. The system of claim 47 wherein the base unit means includes programming means for enabling the user to direct at least one of the sound producing means and the visual display means to make user-selected customized outputs.

51. The system of claim 44 wherein the base unit means includes programming means for enabling the user to direct the indicating means to make user-selected customized indications.

52. The system of claim 44 wherein the monitor means has a plurality of operating modes and wherein one of said operating modes is a range determining mode whereby said monitor means transmits radio frequency signals which cause the indicating means to indicate how well the base unit means is receiving said radio frequency signals when said monitor means is at various locations away from said base unit means.

53. The system of claim 52 wherein the monitor means includes activation means manually operable by the user of said monitor means for at least one of activating and deactivating the range determining mode.

54. The system of claim 53 wherein the transmitting means transmits radio frequency signals continuously while the monitor means is in the range determining mode.

55. The system of claim 52 wherein the indicating means includes sound producing means to broadcast sounds which indicate how well the base unit means is receiving the radio frequency signals of the monitor means when said monitor means is in the range determining mode.

56. The system of claim 55 wherein the base unit means varies the output of the sound producing means according to the strength of the radio frequency signals that said base unit means receives from the monitor means.

57. The system of claim 44 wherein the base unit means includes diagnostic means for determining a problem with the operation of said base unit means and wherein said diagnostic means causes the indicating means to indicate any said problem.

58. The system of claim 29 wherein the monitor means includes notifying means for providing an indication at the immediate location of said monitor means when said monitor means determines that the user of said monitor means has a specified heart condition problem and the base unit means includes indicating means for providing an indication in a proximate surrounding area of said base unit means when the radio frequency signals transmitted by said monitor means are one of unreceived by said base unit means and received by said base unit means and user.

59. The system of claim 58 wherein said system selectively issues warnings in at least three zone: at the immediate location of the monitor means via the notifying means, in a proximate surrounding area of the base unit means via the indicator means, and at a location remote from the larger surrounding area of said base unit means via the message delivery means.

60. The system of claim 59 wherein both the notifying means and the indicating means include sound producing means to broadcast at least one audible sound.

61. The system of claim 60 wherein the message delivery means, the notifying means, and the indicating means immediately summon assistance when the monitor means determines that the user of said monitor means has a specified heart condition problem and wherein the sound producing means associated with said indicating means later broadcasts sounds intermittently to allow rescuers to home in one the sound broadcast by the sound producing means associated with said notifying means.

62. The system of claim 61 wherein the sound producing means associated with the indicating means broadcasts verbal messages.

63. The system of claim 59 wherein the base unit means includes information giving means for providing emergency instructions and information to a caregiver in the event of a downturn in the physiological condition of the user of the monitor means.

64. The system of claim 58 wherein both the monitor means and the base unit means have diagnostic means for determining an operational problem in said system, whereby the diagnostic means associated with said monitor means causes the transmitting means to transmit at least one radio frequency signal indicative of an operational problem in said monitor means and causes the notifying means to indicate any said operational problem and whereby the diagnostic means associated with said base unit means causes the indicating means to indicate a problem with the operation of said base unit means.

65. The system of claim 58 wherein the base unit means includes programming means for enabling the user to direct the indicating means to make user-selected customized indications.

66. The system of claim 58 wherein the monitor means has a plurality of operating modes and wherein one of said operating modes is a range determining mode whereby said monitor means transmits radio frequency signals which cause the indicating means associated with the base unit means to indicate how well said base unit means is receiving said radio frequency signals when said monitor means is at various locations away from said base unit means.

67. The system of claim 66 wherein the indicating means includes sound producing means to broadcast sounds which indicate how well the base unit means is receiving the radio frequency signals of the monitor means when said monitor means is in the range determining mode.

68. The system of claim 67 wherein the base unit means varies the output of the sound producing means according to the strength of the radio frequency signals that said base unit means receives from the monitor means.

69. The system of claim 58 wherein the monitor means prioritizes any detected operational condition and user heart condition and wherein the notifying means and the indicating means indicate only the most important said condition according to a predetermined priority whenever said monitor means determines that more than one said condition exists and should be indicated by said systems.

70. The system of claim 58 wherein the notifying means and the indicating means provide in indication that the message delivery means is about to deliver its message a short time before said message delivery means actually begins to deliver its message, thereby allowing a user to deactivate said message delivery means.

71. The system of claim 59 wherein the monitor means includes activation means manually operable by the user of said monitor means for causing the transmitting means to transmit at least one radio frequency signal indicative of a user desire to deactivate the message delivery means, said radio frequency signal causing the base unit means to deactivate said message delivery means.

72. The system of claim 58 wherein the monitor means includes activation means manually operable by the user of said monitor means for causing the transmitting means to transmit at least one predetermined radio frequency signal indicative of a user diagnosed heart condition problem and causing the notifying means to indicate any said heart condition problem, said radio frequency signal causing the indicating means associated with the base unit means to indicate said problem.

73. The system of claim 9 wherein the base unit means includes control means for at least one of activating and deactivating other household devices to which said base unit means is connected.

74. The system of claim 73 wherein the monitor means includes activation means manually operable by the user of said monitor means for causing the transmitting means to transmit at least one radio frequency signal indicative of a user desire to at least one of activate and deactivate other household devices to which the base unit means is connected, said radio frequency signal causing said base unit means to at least one of activate and deactivate said other household devices.

75. The system of claim 9 wherein the base unit means can interpret and process radio frequency signals from a plurality of monitor means.

76. The system of claim 75 wherein each of a plurality of monitor means transmits individually coded radio frequency signals, thereby enabling a base unit means to identify and distinguish each said monitor means when said base unit means receives radio frequency signals from a plurality of said monitor means.

77. The system of claim 76 wherein a base unit means can make different specialized outputs for each of a plurality of monitor means which sends said base unit means radio frequency signals.

78. The system of claim 9 wherein the monitor means includes defibrillatory sensing means for detecting a defibrillatory electrical shock that the user of said monitor means receives and wherein said defibrillatory sensing means causes the transmitting means to transmit at least one radio frequency signal indicative of the detection of said defibrillatory electrical shock.

79. The system of claim 78 wherein the defibrillatory sensing means includes at least one stainless steel electrode.

80. The system of claim 29 wherein the base unit means includes information giving means for providing emergency instructions and information to a caregiver in the event of a downturn in the physiological condition of the user of the monitor means.

81. The system of claim 80 wherein the information giving means is removable from the base unit means and is portable so that said information giving means can provide emergency instructions and information to a caregiver at a location remote from said base unit means.

82. The system of claim 81 wherein the information giving means includes powering means for providing power to said information giving means, said powering means comprising at least one rechargeable battery.

83. The system of claim 82 wherein the base unit means includes charging means for charging the powering means.

84. The system of claim 80 wherein the information giving means includes sound producing means for selectively broadcasting a reproduction of at least one predetermined audible message.

85. The system of claim 84 wherein the information giving means includes activation means manually operable by a caregiver for at least one of activating and deactivating the information giving means.

86. The system of claim 85 wherein the activation means includes repeating means for causing the information giving means to repeat at least a portion of its audible message and ready means for causing said information giving means to broadcast the next audible instruction in a series.

87. The system of claim 84 wherein the information giving means broadcasts verbal instructions on how to perform cardiopulmonary resuscitation.

88. The system of claim 84 wherein the information giving means includes repository means for storing digital data representative of at least one verbal message and converting means for converting said digital data to an analog form suitable for verbal broadcast.

89. The system of claim 74 wherein the monitor means includes activation means manually operable by the user of said monitor means for at least one of activating and deactivating at least parts of said system.

90. The system of claim 89 wherein the monitor means has at least two operating modes and wherein the activation means enables the user to switch said monitor means between at least the first and second operating modes, whereby said monitor means performs all of its operations when in said first operating mode and suspends some of its operations when in said second operating mode.

91. The system of claim 90 wherein the sensing means suspends its monitoring of the heart condition of the user when the monitor means is in the second operating mode.

92. The system of claim 89 wherein the activation means causes the transmitting means to transmit at least one predetermined radio frequency signal indicative of at least one of a user-diagnosed heart condition problem, a user-diagnosed non-heart condition emergency situation, and a user desire to suspend at least some operations of the base unit means.

93. The system of claim 92 wherein the message delivery means can deliver at least one message indicating a problem other than a user heart condition problem that was automatically detected by the monitor means, said message varying depending on the particular radio frequency signal received by the base unit means.

94. The system of claim 92 wherein the base unit means will immediately suspend at least part of its operations if said base unit means receives a radio frequency signal from the monitor means indicative of a user desire to suspend the operations of said base unit means.

95. The system of claim 92 wherein the monitor means includes notifying means to indicate a user-diagnosed problem at the immediate location of said monitor means and wherein the base unit means includes indicating means to indicate said user-diagnosed problem in a proximate surrounding area of said base unit means.

96. The system of claim 89 wherein the monitor means has a plurality of operating modes and wherein said monitor means operates in a different said operating mode depending on the number of times that the activation means are actuated by the user.

97. The system of claim 89 wherein the activation means includes plurality of user-actuated switching means and wherein each said switching means activates a different operation in the monitor means.

98. The system of claim 97 wherein the monitor means includes prioritizing means for enabling said monitor means to make a preferred response when a plurality of the switching means are pressed during a defined time interval.

99. The system of claim 89 wherein the monitor means includes cover means for protecting at least part of the activation means from at least one of damage and accidental actuation.

100. The system of claim 99 wherein the cover means includes a hinged door which can be opened and closed by the user of the monitor means.

101. The system of claim 9 wherein the base unit means includes modem means for sending electronic data indicative of the operation of said system to at least one location remote from said base unit means via the message delivery means through said telephone network.

102. The system of claim 101 wherein the base unit means includes information storage means for storing information about the operation of said system and for converting said information to electronic data suitable for transfer via the modem means.

103. The system of claim 102 wherein the modem means sends electronic data specifying at least one of the frequency of use of said system, each specific radio frequency signal of the monitor means that was received by the base unit means, and the operating status of said system.

104. The system of claim 103 wherein the electronic data specifies when each electronic data record was originally recorded and stored by the base unit means.

105. The system of claim 103 wherein the electronic data specifies each heart condition measurement of the user that was recorded by said system.

106. The system of claim 101 wherein the modem means sends electronic data to a processing means and wherein said processing means compiles and processes all of said electronic data.

107. The system of claim 101 wherein the base unit means includes programming means for enabling a user to direct the modem means to send electronic data to at least one user-selected location at at least one user-selected time.

108. The system of claim 9 wherein the base unit means includes programming means for enabling the user to direct said base unit means to make user-selected customized outputs.

109. The system of claim 108 wherein the programming means can direct the message delivery means to deliver a user-selected sequence of messages to specified locations remote from the base unit means.

110. The system of claim 108 wherein the base unit means includes sound producing means to broadcast at least one user-selected customized verbal message.

111. The system of claim 110 wherein the base unit means includes repository means for storing digital data representative of at least one verbal message and converting means for converting said digital data to an analog form suitable for verbal broadcast.

112. The system of claim 108 wherein the base unit means modem means for sending electronic data indicative of the operation of said system to at least one user-selected location remote from the base unit means.

113. The system of claim 108 wherein the programming means includes input means for enabling the user to enter in desired messages and information and includes instruction means for providing instructions to help said user enter in the desired messages and information.

114. The system of claim 113 wherein the input means includes keypad means for entering in numbers and alphabetical characters and microphone means for recording verbal messages and wherein the instruction means includes display means for providing visual instructional messages and sound producing means for providing verbal instructions.

115. The system of claim 9 wherein the sensing means includes infrared emitting means and infrared detecting means.

116. The system of claim 115 wherein the infrared emitting means and the infrared detecting means monitor the capillary blood flow of the user.

117. A system for monitoring the blood flow status of a user and alerting people to a user heart condition problem when the blood flow status of said user indicates such as problem, comprising:

portable monitor means worn on the arm of the user for monitoring heart conditions of the user and comprising sensing means actuated by said monitor means for sensing the blood flow status of said user, said sensing means comprising an infrared emitter and an infrared detector, and transmitting means actuated by said monitor means for transmitting at least one radio frequency signal indicative of the sensed blood flow status of said user;

base unit means for receiving said radio frequency signals from said monitor means and selectively generating an output indication signal when said radio frequency signals indicate a user heart condition problem, said base unit means physically separate from said monitor means; and message delivery means connectable to a telephone network and associated with and actuated by said output indication signal of said base unit means for automatically delivering at least one message indicative of a user heart condition problem on said telephone network for summoning emergency assistance when said radio frequency signals indicate said user blood flow status problem.

118. The system of claim 117 wherein the sensing means monitors the capillary blood flow of the user.

119. The system of claim 117 wherein the sensing means includes a plurality of infrared light emitters and a plurality of infrared light detectors to enable the monitor means to accurately determine the blood flow status of the user of said monitor means when said monitor means is at various positions on the arm of said user.

120. The system of claim 119 wherein only one infrared light emitter is energized during each attempt by the sensing means to monitor the blood flow status of the user and wherein a plurality of infrared light emitters are energized if the monitor means cannot detect the blood flow of said user within a short time after said monitor means expected to detect said blood flow.

121. The system of claim 117 wherein the monitor means includes control means for minimizing the power requirements of the sensing means when said sensing means is sensing the blood flow status of the user.

122. The system of claim 121 wherein the control means activates the sensing means intermittently.

123. The system of claim 121 wherein the sensing means includes a plurality of infrared light emitters and wherein the control means energizes only one said infrared light emitter to monitor the blood flow status of the user during normal blood flow detection.

124. The system of claim 121 wherein the control means causes the infrared emitter to emit infrared light in a partial duty cycle when energized.

125. The system of claim 121 wherein the monitor means includes light transporting means for transporting the infrared light emitted by a single infrared light emitter to a plurality of locations on the skin of the user.

126. The system of claim 125 wherein the light transporting means includes at least one optical fiber.

127. The system of claim 117 wherein the monitor means includes determining means for determining the blood flow status of the user of said monitor means from the information provided by the sensing means and wherein said determining means causes the transmitting means to transmit at least one radio frequency signal indicative of a user cardiac arrest if said determining means determines any said cardiac arrest.

128. The system of claim 117 wherein the sensing means determines that the user has a cardiac arrest only if said sensing means fails to detect any user blood flow during a specified time period.

129. The system of claim 128 wherein the specified time period is the time interval required for the sensing means to sense the blood flow status of the user at least three consecutive times.

130. The system of claim 117 wherein the monitor means transmits radio frequency signals indicative of all of the blood flow status information of the user provided by the sensing means when said sensing means is sensing the blood flow status of said user.

131. The system of claim 130 wherein the monitor means transmits radio frequency signals containing information on more than one sensing attempt by the sensing means, said radio frequency signals being transmitted less frequently than said sensing means senses the blood flow status of the user.

132. The system of claim 130 wherein the monitor means transmits radio frequency signals indicative of each instantaneous blood flow measurement of the user that is detected by the sensing means.

133. The system of claim 130 wherein the monitor means transmits radio frequency signals indicative of one of a normal user heart condition and a cardiac arrest.

134. The system of claim 117 wherein the monitor means transmits radio frequency signals indicative of one of a normal user heart condition and a cardiac arrest.

135. A system for monitoring blood flow status of a user and alerting people to a user heart condition problem when the blood flow status of said user indicates such a problem, comprising:
  monitor means for monitoring the blood flow status of the user and transmitting signals indicative of said blood flow status, said monitor means worn on the arm of said user and portable, said monitor means comprising: sensing means actuated by said monitor means for sensing the blood flow status of said user, said sensing means comprising an infrared emitter and an infrared detector; notifying means selectively actuated by said monitor means for providing an indication at the immediate location of said monitor means when said monitor means determines that the user has a specified blood flow status problem; and transmitting means selectively actuated by said monitor means for transmitting at least one radio frequency signal indicative of the sensed blood flow status of said user;
  base unit means for receiving said radio frequency signals from said monitor means and selectively generating an output indication signal in responses to said radio frequency signals, said base unit means physically separate from said monitor means;
  indicating means associated with and actuated by said output indication signal of said base unit means for providing an indication in a proximate surrounding area of said base unit means when said radio frequency signals transmitted by said monitor means are one of unreceived by said base unit means and received by said base unit means and indicative of a specified blood flow status of said user; and
  message delivery means adapted for connection to a telephone network and associated with and actuated by said base unit means for automatically delivering at least one message indicative of a user heart condition problem on said telephone network for summoning emergency assistance when said radio frequency signals indicate said user blood flow status problem.

136. The system of claim 135 wherein said system selectively issues warnings in at least three zones: at the immediate location of the monitor means via the notifying means, in said proximate surrounding area of the base unit means via the indicating means, and at a location remote from said base unit means and said monitor means via the message delivery means.

137. The system of claim 136 wherein both the notifying means and the indicating means include sound producing means to broadcast at least one audible around.

138. The system of claim 137 wherein the message delivery means, the notifying means, and the indicating means immediately summon assistance when the monitor means determines that the user of said monitor means has a specified blood flow status problem and wherein the sound producing means associated with said indicating means later broadcasts sounds intermittently to allow rescuers to home in one the sound broadcast by the sound producing means associated with said notifying means.

139. The system of claim 138 wherein the sound producing means associated with the indicating means broadcasts verbal messages.

140. The system of claim 139 wherein the base unit means includes repository means for storing digital data representative of at least one verbal message and converting means for converting said digital data to an analog form suitable for verbal broadcast.

141. The system of claim 137 wherein both the notifying means and the indicating means include visual display means to display at least one visible message.

142. The system of claim 135 wherein the monitor means includes attachment means for securing said monitor means to the arm of the user and also includes attachment sensing means for determining the attachment status of said attachment means with respect to said arm of said user.

143. The system of claim 142 wherein the monitor means has at least two operating modes, operating in a first operating mode when the attachment sensing means determines a secured attachment status of the attachment means and operating in a second operating mode when said attachment sensing means determines an unsecured attachment status of said attachment means, and whereby said attachment sensing means causes the notifying means to indicate said unsecured attachment status and causes the transmitting means to transmit at least one radio frequency signal indicative of said unsecured attachment status, said radio frequency signal causing the indicating means to indicate said unsecured attachment status.

144. The system of claim 142 wherein said attachment sensing means is connected to said transmitting means and said transmitting means further operates to signal said attachment status to said monitor means.

145. The system of claim 135 wherein both the monitor means and the base unit means have diagnostic means for determining an operational problem in said system, whereby the diagnostic means associated with said monitor means causes the transmitting means to transmit at least one radio frequency signal indicative of an operational problem in said monitor means and causes the notifying means to indicate any said operational problem and whereby the diagnostic means associated with said base unit means causes the indicating means to indicate a problem with the operation of said base unit means.

146. The system of claim 145 wherein the diagnostic means associated with the base unit means includes telephone line surveillance means for determining and operational problem in the telephone line to which said base unit means is connected.

147. The system of claim 145 wherein the diagnostic means associated with the monitor means includes charge determining means for determining the charge status of any batteries powering said monitor means.

148. The system of claim 135 wherein the monitor means prioritizes any detected operational condition and user blood flow status condition and wherein the notifying means and the indicating means indicate only the most important said condition according to a predetermined priority whenever said monitor means determines that more than one said conditions exists and should be indicated by said system.

149. The system of claim 135 wherein the monitor means includes activation means manually operable by the user of said monitor means for at least one of activating and deactivating at least parts of said system.

150. The system of claim 149 wherein the monitor means has at least two operating modes and wherein the activation means enables the user to switch said monitor means between at least the first and second operating modes, whereby said monitor means performs all of its operations when in said first operating mode and suspends some of its operations when in said second operating mode.

151. The systme of claim 150 wherein the sensing means suspends its monitoring of the blood flow sustatus of the user when the mointor means is in the second operating mode.

152. The system of claim 149 wherein the activation means causes the transmitting means to transmit at least one predetermined radio frequency signal indicative of at least one of a user-diagnosed heart condition problem, a user-diagnosed non-heart condition emergency situation, and a user desire to suspend at least some operations of the base unit means.

153. The system of claim 152 wherein each of the notifying means and the indicating means can indicate a user-diagnosed problem and wherein the message delivery means can deliver at least one message indicating a problem other than a user heart condition problem that was automatically detected by the monitor means, said message varying depending on the particular radio frequency signal received by the base unit means.

154. The system of claim 152 wherein the base unit means will immediately suspended at least part of its operations if said base unit means receives a radio frequency signal from the monitor means indicative of a user desire to suspended the operations of said base unit means.

155. The system of claim 154 wherein the notifying means and the indicating means provide an indication that the message delivery means is about to deliver its message a short time before said message delivery means actually begins to deliver its message, thereby allowing a user to deactivate said message delivery means by utilizing the activation means.

156. The system of claim 135 wherein the message delivery means includes sound producing means for delivering at least one audible message to at least one location remote from the surrounding area of the base unit means through said telephone network.

157. The system of claim 135 wherein the monitor means has a plurality of operating modes and wherein one of said operating modes is a range determining mode whereby said monitor means transmits radio frequency signals which cause the indicating means to indicate how well the base unit means is receiving said radio frequency signals when said monitor means is at various locations away from said base unit means.

158. The system of claim 157 wherein the monitor means includes activation means manually operable by the user of said monitor means for at least one of activating and deactivating the range determining mode.

159. The system of claim 158 wherein the transmitting means transmits radio frequency signals continuously while the monitor means is in the range determining mode.

160. The system of claim 157 wherein the indicating means includes sound producing means to broadcast sounds which indicate how well the base unit means is receiving the radio frequency signals of the monitor means when said monitor means is in the range determining mode.

161. The system of claim 160 wherein the base unit means varies the output of the sound producing means according to the strength of the radio frequency signals that said base unit means receives from the monitor means.

162. The system of claim 135 wherein the base unit means includes control means for at least one of activating and deactivating other household devices to which said base unit means is connected.

163. The system of claim 162 wherein the monitor means includes activation means manually operable by the user of said monitor means for causing the transmitting means to transmit at least one radio frequency signal indicative of a user desire to at least one of activate and deactivate other household devices to which the base unit means is connected, said radio frequency signal causing said base unit means to at least one of activate and deactivate said other household devices.

164. The system of claim 135 wherein the base unit means can interpret and process radio frequency signals from a plurality of monitor means.

165. The system of claim 164 wherein each of a plurality of monitor means transmits individually coded radio frequency signals, thereby enabling a base unit means to identify and distinguish each said monitor means when said base unit means receives radio frequency signals from a plurality of said monitor means.

166. The system of claim 165 wherein a base unit means can make different specialized outputs for each of a plurality of monitor means which sends said base unit means radio frequency signals.

167. The system of claim 135 wherein the monitor means includes defibrillatory sensing means for detecting a defibrillatory electrical shock that the user of said monitor means receives and wherein said defibrillatory sensing means causes the transmitting means to transmit at least one radio frequency signal indicative of the detection of said defibrillatory electrical shock.

168. The system of claim 167 wherein the defibrillatory sensing means includes at least one stainless steel electrode.

169. The system of claim 135 wherein the base unit means includes information giving means for providing emergency instructions and information to a caregiver in the event of a downturn in the physiological condition of the user of the monitor means.

170. The system of claim 169 wherein the information giving means is removable from the base unit means and is portable so that said information giving means can provide emergency instructions and information to a caregiver at a location remote from said base unit means.

171. The system of claim 170 wherein the information giving means includes powering means for providing power to said information giving means, said powering means comprising at least one rechargeable battery.

172. The system of claim 171 wherein the base unit means includes charging means for charging the powering means.

173. The system of claim 169 wherein the information giving means includes sound producing means for selectively broadcasting a reproduction of at least one predetermined audible message.

174. The system of claim 173 wherein the information giving means includes activation means manually operable by a caregiver for at least one of activating and deactivating the information giving means.

175. The system of claim 174 wherein the activation means includes repeating means for causing the information giving means to repeat at least a portion of its audible message and ready means for causing said information giving means to broadcast the next audible instruction in a series.

176. The system of claim 173 wherein the information giving means broadcasts verbal instructions on how to perform cardiopulmonary resuscitation.

177. The system of claim 173 wherein the information giving means includes repository means for storing digital data representative of at least one verbal message and converting means for converting said digital data to an analog form suitable for verbal broadcast.

178. The system of claim 135 wherein the base unit means includes modem means for sensing electronic data indicative of the operation of said system to at least one location remote from said base unit means via the message delivery means.

179. The system of claim 178 wherein the base unit means includes information storage means for storing information about the operation of said system and for converting said information to electronic data suitable for transfer via the modem means.

180. The system of claim 179 wherein the modem means sends electronic data specifying at least one of the frequency of use of said system, each specific radio frequency signal of the monitor means that was received by the base unit means, and the operating status of said system.

181. The system of claim 180 wherein the electronic data specifies when each electronic data record was originally recorded and stored by the base unit means.

182. The system of claim 180 wherein the electronic data specifies each actual instantaneous blood flow measurement of the user that was recorded by said system.

183. The system of claim 178 wherein the modem means sends electronic data to a processing means and wherein said processing means compiles and processes all of said electronic data.

184. The system of claim 135 wherein the base unit means includes programming means for enabling the user to direct said base unit means to make user-selected customized outputs.

185. The system of claim 184 wherein the programming means can direct the message delivery means to deliver a user-selected sequence of messages to specified locations remote from the base unit means.

186. The system of claim 184 wherein the base unit means includes sound producing means to broadcast at least one user-selected customized verbal message.

187. The system of claim 184 wherein the base unit means includes modem means for sending electronic data indicative of the operation of said system to at least one user-selected location remote from said base unit means at at least one user-selected time via the message delivery means.

188. The system of claim 184 wherein the programming means includes input means for enabling the user to enter in desired messages and information and includes instruction means for providing instructions to help said user enter in the desired messages and information.

189. The system of claim 188 wherein the input means includes keypad means for entering in numbers and alphabetical characters and microphone means for recording verbal messages and wherein the instruction means includes display means for providing visual instructional messages and sound producing means for providing verbal instructions.

190. The system of claim 135 wherein the monitor means includes powering means for providing power to said monitor means, said powering means including at least one rechargeable battery.

191. The system of claim 190 wherein the base unit means includes charging means for charging the powering means.

192. A system for monitoring the heart condition of a user and alerting people to a user heart condition problem, comprising:

portable monitor means for monitoring the heart function of said user and transmitting signals indicative of said heart condition, said monitor means comprising: control means for controlling the operation of the monitor means and determining the existence of any heart condition problem; sensing means connected to and actuated by said control means for sensing the heart condition of said user; diagnostic means connected to said control means for detecting and signalling an operational problem in said monitor means; attachment means for securing said monitor means to the arm of said user; attachment sensing means connected to said attachment means and to said control means for determining and signalling the attachment status of said attachment means with respect to the arm of said user; transmitting means connected to and actuated by said control means for transmitting radio frequency signals indicative of at least one of the sensed heart condition of said user and the operating status of said monitor means; activation means connected to said control means and manually operable by said user for at least one of activating a specified operating status of said monitor means and causing said transmitting means to transmit a predetermined radio frequency signal; and notifying means associated with and actuated by said monitor means for providing an indication at the immediate location of said monitor means when said monitor means determines that said user has a specified heart condition problem said notifying means providing in response at least one of a visual and audible indication;

base unit means for receiving said radio frequency signals from said monitor means analyzing said signals, and selectively producing an output signal upon determination of said user heart condition problem, said base unit means being physically separate from said monitor means and comprising: diagnostic means for determining a problem with the operation of said base unit means; indicating means actuated by said output signal of said base unit means for providing an indication in a surrounding area of said base unit means when said radio frequency signals transmitted by said monitor means are one of unreceived by said base unit means, and received by said base unit means and indicative of a specified heart condition problem of said user, said indicating means providing in response at least one of a visual and an audible indication information giving means for providing emergency instructions and information to a caregiver in the event of a downturn in the physiological condition of said user, said information giving means providing verbal instructions on performance of cardiac resuscitation; programming means associated with said base unit means for enabling said user to direct said base unit means to make user-selected customized outputs; and message delivery means associated with and actuated by said base unit means for automatically delivering at least one message on a telephone network, said message being at least one of a prerecorded verbal message indicating a user heart condition problem and summoning emergency assistance when said radio frequency signals indicate said user heart condition problem, and electronic data indicating the operation of said system.

193. A system for monitoring the blood flow status of a user and alerting people to a user heart condition problem when the blood flow status of said user indicates such as problem, comprising:
portable monitor means for monitoring blood flow and transmitting indications of sensed conditions and worn on a limb of said user said monitoring means comprising:
control means for controlling monitoring and transmitting functions of said monitor means;
sensing means connected to and actuated by said control means for sensing the blood flow status of said user and determining any user blood flow status problem, said sensing means and comprising an infrared emitter and an infrared detector;
diagnostic means connected to said control means for detecting and signalling an operational problem in said monitor means;
attachment means for securing said monitor means to the limb of said user;
attachment sensing means connected to said attachment means and said control means for determining and signalling the attachment status of said attachment means with respect to the limb of said user;
transmitting means connected to and actuated by said control means for transmitting radio frequency signals indicative of the sensed blood flow status of said user and the operating status of said monitor means;
activation means connected to said control means manually operable by said user for at least one of activating a specified operating status of said monitor means and causing said transmitting means to transmit a predetermined radio frequency signal; and
notifying means associated with and selectively actuated by said control means for providing an indication at the immediate location of said monitor means when said monitor means determines that said user has a specified blood flow status and said monitor means operates in a specified operating status, said notifying means including at least one of an audible and a visual signal producing device;
base unit means for receiving and said radio frequency signals from said monitor means and analyzing said signals;
diagnostic means associated with said base unit means for determining and signalling a problem with the operation of said base unit means;
indicating means associated with and actuated by said base unit means for providing an indication in a proximate surrounding area of said base unit means when said radio frequency signals transmitted by said monitor means are one of unreceived by said base unit means, and received by said base unit means and indicative of a specified blood flow status of said user, said indicating means including at least one of an audible and a visual indicator;
information giving means associated with said base unit means for providing emergency instructions and information to a caregiver in the event of a downturn in the physiological condition of said user, said information giving means providing verbal instructions on performance of cardiac resuscitation;
programming means associated with said base unit means for enabling said user to direct said base unit means to make user-selected customized outputs; and
message delivery means associated with and actuated by said base unit means for automatically delivering at least one message an a telephone network, said messgae being at least one of a prerecorded verbal message indicating a user heart condition problem and summoning emergency assistance when said radio frequency signals indicate said user blood flow status problem, and electronic data indicating the operation of said system.

194. A system for monitoring the blood flow status of a user and alerting people to a user heart condition problem when the blood flow status of said user indicates such as problem, comprising:
portable monitor means for monitoring blood flow status of the user and transmitting data signals indicative of said blow flow status, said monitor means worn on the arm of said user and comprising:
control means for controlling monitoring and transmitting functions of said monitor means;
sensing means associated with and actuated by said control means for sensing the blood flow status of said user, said sensing means comprising an infrared emitter and an infrared detector;
diagnostic means connected to said control means for determining and signalling an operational problem in said monitor means;
attachment menas for securing said monitor means to the arm of said user;

attachment sensing means associated with said attachment means and connected to said attachment means and to said control means for determining the attachment status of said attachment means with respect to the arm of said user;

transmitting means associated with and actuated by said control means for transmitting radio frequency signals indicative of the blood flow status of said user and the operating status of said monitor means;

manual activation means connected to said control means and manually operable by said user for activating a specified operating status of said monitor means and causing said transmitting means to transmit a predetermined radio frequency signal; and notifying means associated with and selectively actuated by said control means for providing an indication at the immediate location of said monitor means when said monitor means determines that said user has a specified blood flow status and said monitor means operates in a specified operating status, said notifying means providing at least one of an audible signal and a visual signal;

base unit means physically separate from said monitoring means for receiving said radio frequency signals from said monitor means and analyzing and responding to said signals;

diagnostic means associated with said base unit means for determining and signalling a problem with the operation of said base unit means;

indicating means associated with and actuated by said base unit means for providing an indication in a proximate surrounding area of said base unit means when said radio frequency signals transmitted by said monitor means are one of unreceived by said base unit means, received by said base unit means and indicative of a specified blood flow status problem of said user, and received by said base unit means and indicative of a specified operating status of said monitor means, said indicating means including at least one of an audible and a visual indicator for providing the indication; and programming means associated with said base unit means for enabling said user to direct said indicating means to make user-selected customized indications.

195. The system of claim 194 wherein the base unit means includes information giving means for providing emergency instructions and information to a caregiver in the event of a downturn in the physiological condition of the user of the monitor means, said information giving means providing verbal instructions on at least how to perform cardiopulmonary resuscitation.

196. A device for giving emergency medical instructions, comprising:

sound producing means for selectively broadcasting a reproduction of at least one set of predetermined audible messages to be delivered in a predetermined sequence, said message set comprising instructions for directing a caregiver to perform an emergency medical procedure is real time on a person requiring emergency medical assistance;

repository means for storing information representative of said instructions;

processing means connected to said sound producing means and said repository means for selectively retrieving said information from said repository means; processing said information, and sending said processed information to said sound producing means to cause said broadcast in sequence of said messages in said message set and operable to enter a non-retrieval mode after certain of said messages are broadcast in which mode subsequent messages are not retrieved and broadcast; and ready signal input means manually operable by said caregiver for selectively operating said processing means to end said non-retrieval mode when broadcast of a subsequent message in said message set is desired to thereby cause said sound producing means to broadcast the next message to said caregiver.

197. The device of claim 196 wherein said device includes repeating means for causing the processing means to send a repetition of at least a portion of the instructions to the sound producing means.

198. The device of claim 196 wherein the sound producing means broadcast a plurality of emergency instructions in series and wherein predetermined messages are repeated broadcast automatically during said nonretrieval mode.

199. The device of claim 196 wherein the sound producing means generates instructions for performing cardiopulmonary resuscitation.

200. The device of claim 196 wherein the repository means stores digital data representative of at leave one verbal message and wherein the processing means includes a digital speech processor for converting said digital data to an analog form suitable for verbal broadcast by the sound producing means.

201. The device of claim 196 further including powering means for providing power to said device, said powering means comprising at least one rechargeable battery.

202. A system for monitoring the blood flow status of a user, comprising:

portable monitor means worn on the arm of said user for monitoring blood flow status of said user and transmitting a status signal indicative of said blood flow status, said monitor means comprising sensing means actuated by said monitor means for sensing actual instantaneous blood flow of said user, said sensing means comprising an infrared emitter and an infrared detector; transmitting means associated with and actuated by said monitor means for transmitting at least one radio frequency signal indicative of each sensed blood flow measurement of said user;

base unit means for receiving and analyzing said radio frequency signals, said base unit means being physically separate from said monitor means;

information storage means associated with and actuated by said base unit means for storing each said blood flow measurement indicated by said radio frequency signals;

converting means associated with and actuated by said base unit means for converting the stored pulse rate measurements of said user to signals suitable for transfer on a telephone network; and message delivery means associated with and actuated by said base unit means and comprising a telephone network connection for automatically delivering electronic data indicative of each said pulse rate measurement of said user on said telephone network.

203. The system of claim 202 wherein the base unit means sends electronic data to a processing means and wherein said processing means compiles and processes all of said electronic data.

* * * * *